(12) United States Patent
Gertler et al.

(10) Patent No.: US 7,307,142 B2
(45) Date of Patent: Dec. 11, 2007

(54) LEPTIN ANTAGONISTS

(75) Inventors: Arieh Gertler, Rehovot (IL); Isabelle Callebaut, Favières (FR); Jean Djiane, Verrières le Buisson (FR)

(73) Assignees: Yissum Research and Development Company of the Hebrew University of Jerusalem, Jerusalem (FR); Universités Paris 6 et Paris 7, Paris (FR); Institut Nationale de la Recherche Agronomique (INRA), Paris (FR)

( * ) Notice: Subject to any disclaimer, the term of this patent is extended or adjusted under 35 U.S.C. 154(b) by 43 days.

(21) Appl. No.: 10/996,607

(22) Filed: Nov. 26, 2004

(65) Prior Publication Data

US 2006/0154859 A1    Jul. 13, 2006

(51) Int. Cl.
*A61K 38/00* (2006.01)

(52) U.S. Cl. .......................... 530/300; 436/86; 514/12; 514/773; 435/69.1

(58) Field of Classification Search ................ None
See application file for complete search history.

(56) References Cited

U.S. PATENT DOCUMENTS

| | | |
|---|---|---|
| 6,309,853 B1 | 10/2001 | Friedman et al. |
| 6,399,745 B1 | 6/2002 | Ertl et al. |
| 2004/0048773 A1 | 3/2004 | Cawthorne et al. |
| 2004/0072219 A1 | 4/2004 | Carr et al. |

FOREIGN PATENT DOCUMENTS

| | | | |
|---|---|---|---|
| GB | 2292382 | * | 2/1996 |
| WO | WO 02/062833 | * | 8/2002 |

OTHER PUBLICATIONS

Peelman et al., "Mapping of the leptin binding sites and design of a leptin antagonist" (2004) J. Biol Chem., vol. 279; pp. 4138-4146.
Raver et al., "Comparison of R128Q mutations in human, ovine, and chicken leptois" (2002) General and Comparative Endocrinology, vol. 126, pp. 52-58.
Verploegen et al., "A human leptin mutant induces weight gain in normal mice" (1997) FEBS Letters, vol. 405, pp. 237-240.
Zabeau et al., "Functional analysis of leptin receptor activation using a Janus kinase/signal transducer and activator of transcription complementation assay" (2004) Molecular Endocrinology, vol. 18 No. 1, pp. 150-161.

* cited by examiner

*Primary Examiner*—Lorraine Spector
*Assistant Examiner*—Elly-Gerald Stoica
(74) *Attorney, Agent, or Firm*—Browdy and Neimark, PLLC

(57) ABSTRACT

The invention relates to synthetic leptin antagonists in which at least two amino acid residues of the sequence LDFI/S of the hydrophobic binding site at positions 39-42 of a leptin polypeptide sequence are substituted with different amino acid residues such that the site becomes less hydrophobic, and fragments of said leptin antagonists.

21 Claims, 8 Drawing Sheets

Ovine leptins

L39A/D40A

F41A/I42A

L39A/D40A/F41A

L39A/D40A/F41A/I42A

Figure 1A:
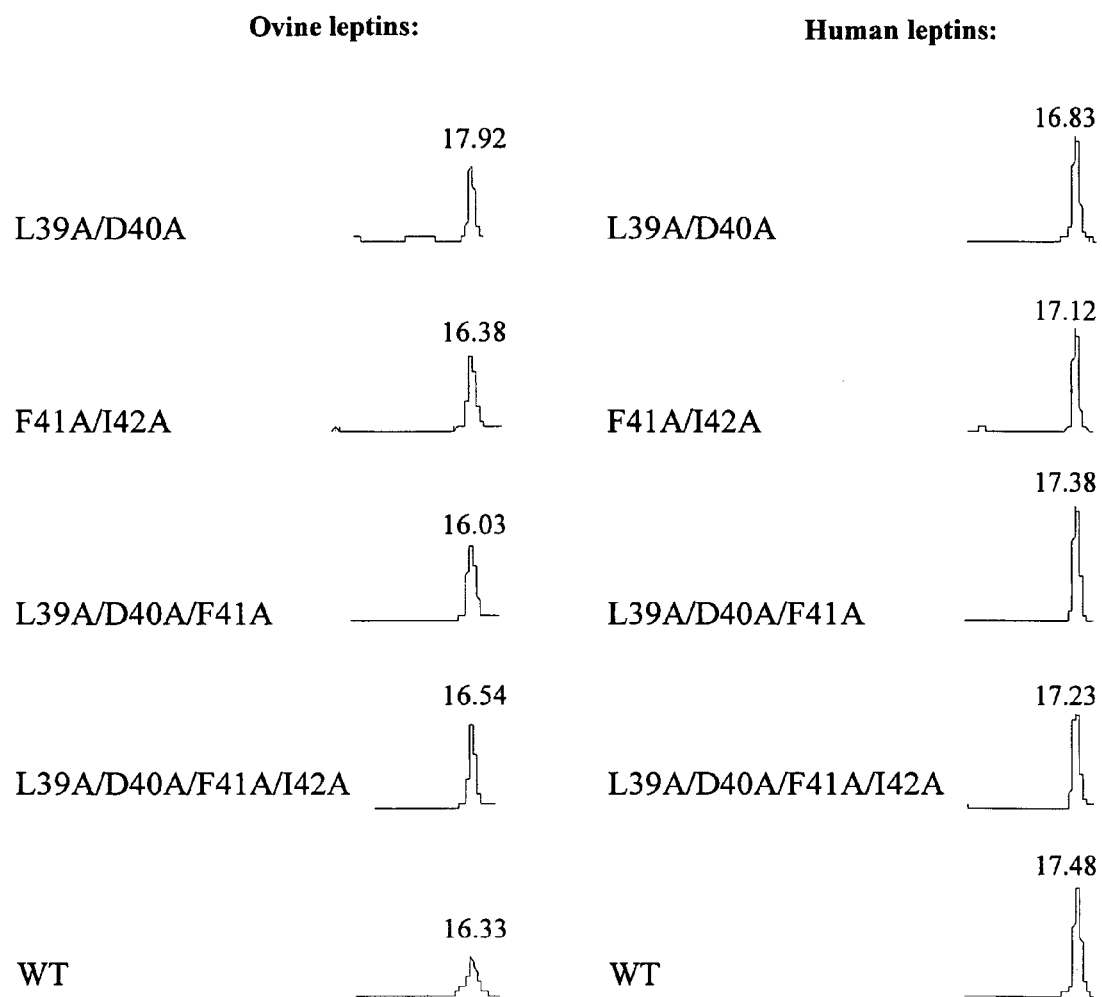
Figure 1B:
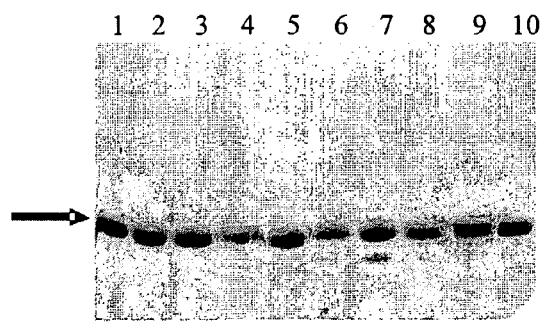
Figure 1C:
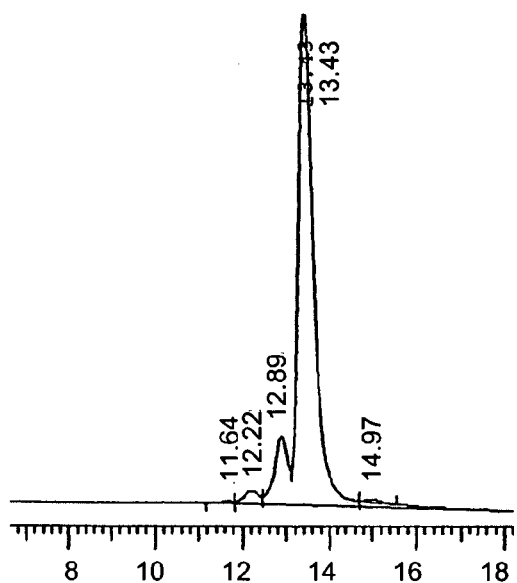
Figure 1C:
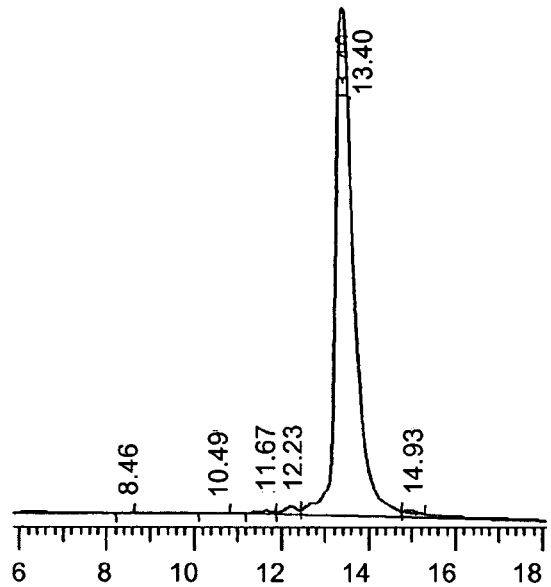
Figure 1C:
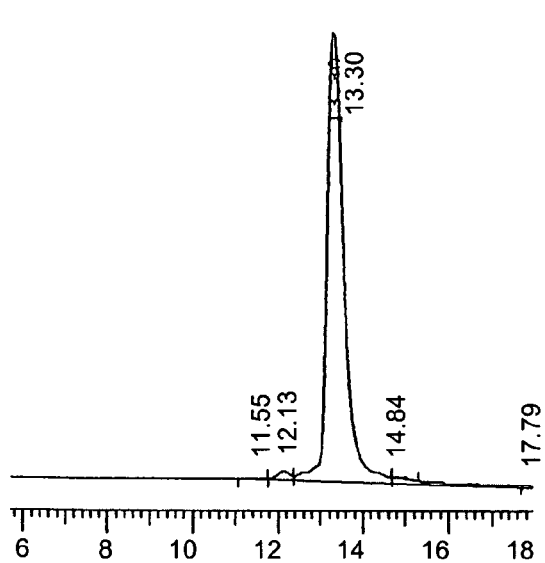
Figure 1C:
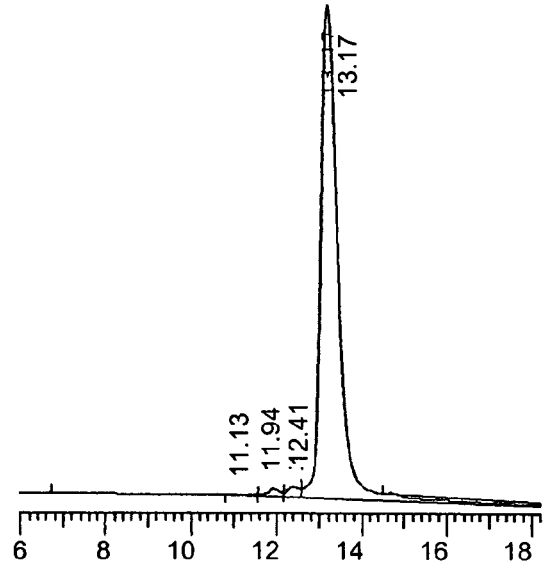

Human leptons
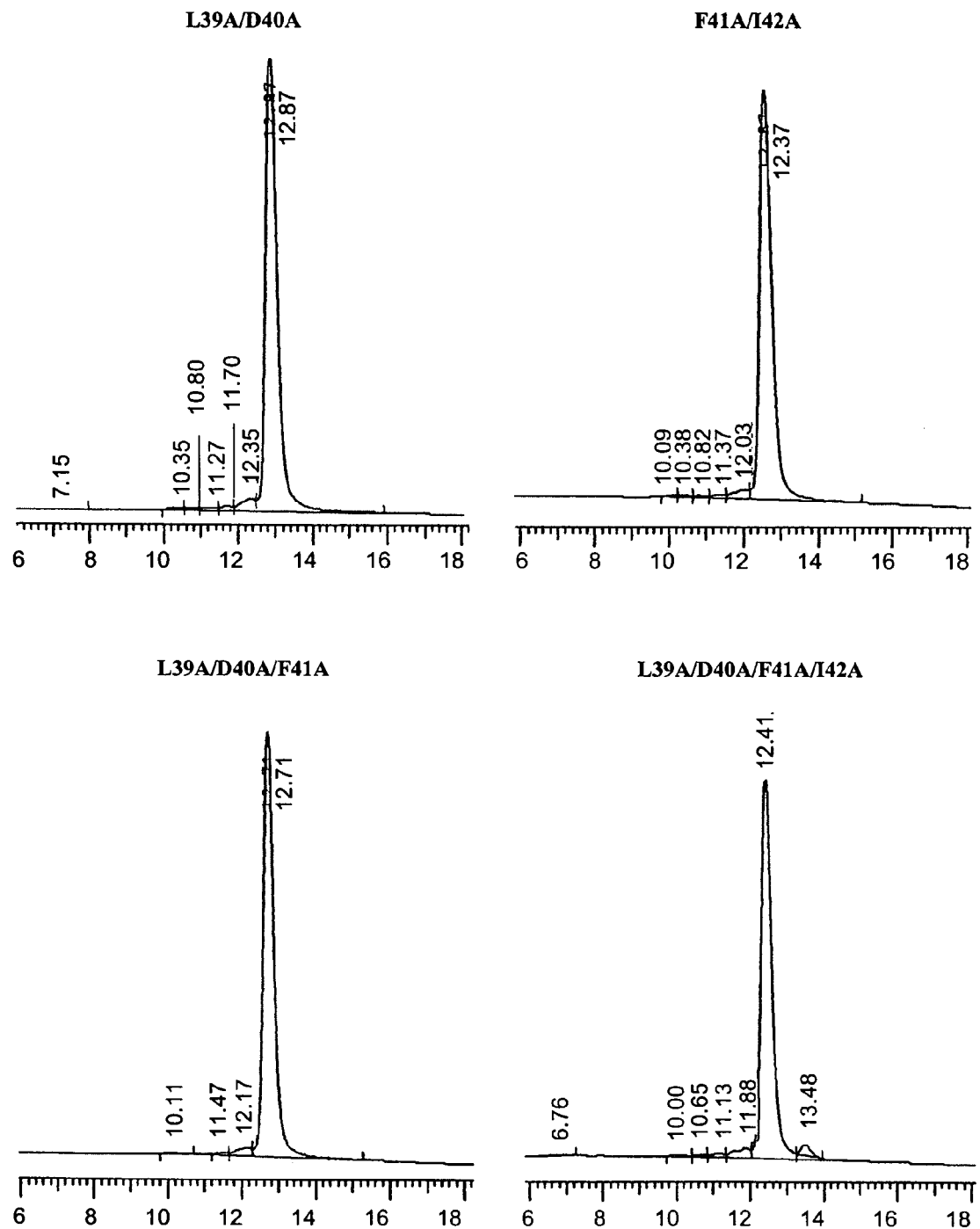
Fig. 1C (Continuation)

SEQUENCE LISTING

```
<160> NUMBER OF SEQ ID NOS: 32

<210> SEQ ID NO 1
<211> LENGTH: 146
<212> TYPE: PRT
<213> ORGANISM: Artificial Sequence
<220> FEATURE:
<223> OTHER INFORMATION: synthetic

<400> SEQUENCE: 1

Val Pro Ile Gln Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser
            20                  25                  30

Lys Gln Lys Val Thr Gly Ala Ala Phe Ile Pro Gly Leu His Pro Ile
        35                  40                  45

Leu Thr Leu Ser Lys Met Asp Gln Thr Leu Ala Val Tyr Gln Gln Ile
    50                  55                  60

Leu Thr Ser Met Pro Ser Arg Asn Val Ile Arg Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
        115                 120                 125

Leu Gln Gly Ser Leu Gln Asp Met Leu Trp Gln Leu Asp Leu Ser Pro
    130                 135                 140

Gly Cys
145

<210> SEQ ID NO 2
<211> LENGTH: 146
<212> TYPE: PRT
<213> ORGANISM: Artificial Sequence
<220> FEATURE:
<223> OTHER INFORMATION: synthetic

<400> SEQUENCE: 2

Val Pro Ile Gln Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser
            20                  25                  30
```

```
Lys Gln Lys Val Thr Gly Leu Asp Ala Ala Pro Gly Leu His Pro Ile
            35                  40                  45

Leu Thr Leu Ser Lys Met Asp Gln Thr Leu Ala Val Tyr Gln Gln Ile
        50                  55                  60

Leu Thr Ser Met Pro Ser Arg Asn Val Ile Arg Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
            115                 120                 125

Leu Gln Gly Ser Leu Gln Asp Met Leu Trp Gln Leu Asp Leu Ser Pro
            130                 135                 140

Gly Cys
145

<210> SEQ ID NO 3
<211> LENGTH: 146
<212> TYPE: PRT
<213> ORGANISM: Artificial Sequence
<220> FEATURE:
<223> OTHER INFORMATION: Synthetic

<400> SEQUENCE: 3

Val Ser Ile Arg Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser
            20                  25                  30

Lys Gln Arg Val Thr Gly Ala Ala Phe Ile Pro Gly Leu His Pro Leu
            35                  40                  45

Leu Ser Leu Ser Lys Met Asp Gln Thr Leu Ala Ile Tyr Gln Gln Ile
        50                  55                  60

Leu Ala Ser Leu Pro Ser Arg Asn Val Ile Gln Ile Ser Asn Asp Leu
65                  70                  75                  80

Glu Asn Leu Arg Asp Leu Leu His Leu Leu Ala Ala Ser Lys Ser Cys
                85                  90                  95

Pro Leu Pro Gln Val Arg Ala Leu Glu Ser Leu Glu Ser Leu Gly Val
            100                 105                 110

Val Leu Glu Ala Ser Leu Tyr Ser Thr Glu Val Val Ala Leu Ser Arg
            115                 120                 125

Leu Gln Gly Ser Leu Gln Asp Met Leu Arg Gln Leu Asp Leu Ser Pro
            130                 135                 140

Gly Cys
145

<210> SEQ ID NO 4
<211> LENGTH: 146
<212> TYPE: PRT
<213> ORGANISM: Artificial Sequence
<220> FEATURE:
<223> OTHER INFORMATION: Synthetic

<400> SEQUENCE: 4

Val Ser Ile Arg Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser
```

```
                    20                  25                  30
Lys Gln Arg Val Thr Gly Leu Asp Ala Ala Pro Gly Leu His Pro Leu
        35                  40                  45

Leu Ser Leu Ser Lys Met Asp Gln Thr Leu Ala Ile Tyr Gln Gln Ile
 50                  55                  60

Leu Ala Ser Leu Pro Ser Arg Asn Val Ile Gln Ile Ser Asn Asp Leu
 65                  70                  75                  80

Glu Asn Leu Arg Asp Leu Leu His Leu Leu Ala Ala Ser Lys Ser Cys
                 85                  90                  95

Pro Leu Pro Gln Val Arg Ala Leu Glu Ser Leu Glu Ser Leu Gly Val
            100                 105                 110

Val Leu Glu Ala Ser Leu Tyr Ser Thr Glu Val Val Ala Leu Ser Arg
        115                 120                 125

Leu Gln Gly Ser Leu Gln Asp Met Leu Arg Gln Leu Asp Leu Ser Pro
    130                 135                 140

Gly Cys
145

<210> SEQ ID NO 5
<211> LENGTH: 146
<212> TYPE: PRT
<213> ORGANISM: Artificial Sequence
<220> FEATURE:
<223> OTHER INFORMATION: Synthetic

<400> SEQUENCE: 5

Val Pro Ile Gln Lys Val Gln Asp Asp Thr Lys Thr Leu Ile Lys Thr
 1               5                  10                  15

Ile Val Thr Arg Ile Asn Asp Ile Ser His Thr Gln Ser Val Ser Ser
                20                  25                  30

Lys Gln Lys Val Thr Gly Ala Ala Ile Pro Gly Leu His Pro Ile
        35                  40                  45

Leu Thr Leu Ser Lys Met Asp Gln Thr Leu Ala Val Tyr Gln Gln Ile
 50                  55                  60

Leu Thr Ser Met Pro Ser Arg Asn Val Ile Arg Ile Ser Asn Asp Leu
 65                  70                  75                  80

Glu Asn Leu Arg Asp Leu Leu His Val Leu Ala Phe Ser Lys Ser Cys
                 85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
        115                 120                 125

Leu Gln Gly Ser Leu Gln Asp Met Leu Trp Gln Leu Asp Leu Ser Pro
    130                 135                 140

Gly Cys
145

<210> SEQ ID NO 6
<211> LENGTH: 146
<212> TYPE: PRT
<213> ORGANISM: Artificial Sequence
<220> FEATURE:
<223> OTHER INFORMATION: Synthetic

<400> SEQUENCE: 6

Val Ser Ile Arg Lys Val Gln Asp Asp Thr Lys Thr Leu Ile Lys Thr
 1               5                  10                  15
```

Ile Val Thr Arg Ile Asn Asp Ile Ser His Thr Gln Ser Val Ser Ser
            20                  25                  30

Lys Gln Arg Val Thr Gly Ala Ala Ala Ile Pro Gly Leu His Pro Leu
            35                  40                  45

Leu Ser Leu Ser Lys Met Asp Gln Thr Leu Ala Ile Tyr Gln Gln Ile
        50                  55                  60

Leu Ala Ser Leu Pro Ser Arg Asn Val Gln Ile Ser Asn Asp Leu
65                  70                  75                  80

Glu Asn Leu Arg Asp Leu Leu His Leu Leu Ala Ala Ser Lys Ser Cys
                85                  90                  95

Pro Leu Pro Gln Val Arg Ala Leu Glu Ser Leu Ser Leu Gly Val
            100                 105                 110

Val Leu Glu Ala Ser Leu Tyr Ser Thr Glu Val Val Ala Leu Ser Arg
            115                 120                 125

Leu Gln Gly Ser Leu Gln Asp Met Leu Arg Gln Leu Asp Leu Ser Pro
        130                 135                 140

Gly Cys
145

<210> SEQ ID NO 7
<211> LENGTH: 146
<212> TYPE: PRT
<213> ORGANISM: Artificial Sequence
<220> FEATURE:
<223> OTHER INFORMATION: Synthetic

<400> SEQUENCE: 7

Val Pro Ile Gln Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser
            20                  25                  30

Lys Gln Lys Val Thr Gly Ala Ala Ala Pro Gly Leu His Pro Ile
            35                  40                  45

Leu Thr Leu Ser Lys Met Asp Gln Thr Leu Ala Val Tyr Gln Gln Ile
        50                  55                  60

Leu Thr Ser Met Pro Ser Arg Asn Val Ile Arg Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
            115                 120                 125

Leu Gln Gly Ser Leu Gln Asp Met Leu Trp Gln Leu Asp Leu Ser Pro
        130                 135                 140

Gly Cys
145

<210> SEQ ID NO 8
<211> LENGTH: 146
<212> TYPE: PRT
<213> ORGANISM: Artificial Sequence
<220> FEATURE:
<223> OTHER INFORMATION: Synthetic

<400> SEQUENCE: 8

Val Ser Ile Arg Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser
                 20                  25                  30

Lys Gln Arg Val Thr Gly Ala Ala Ala Ala Pro Gly Leu His Pro Leu
            35                  40                  45

Leu Ser Leu Ser Lys Met Asp Gln Thr Leu Ala Ile Tyr Gln Gln Ile
        50                  55                  60

Leu Ala Ser Leu Pro Ser Arg Asn Val Ile Gln Ile Ser Asn Asp Leu
65                  70                  75                  80

Glu Asn Leu Arg Asp Leu Leu His Leu Leu Ala Ala Ser Lys Ser Cys
                85                  90                  95

Pro Leu Pro Gln Val Arg Ala Leu Glu Ser Leu Glu Ser Leu Gly Val
            100                 105                 110

Val Leu Glu Ala Ser Leu Tyr Ser Thr Glu Val Val Ala Leu Ser Arg
        115                 120                 125

Leu Gln Gly Ser Leu Gln Asp Met Leu Arg Gln Leu Asp Leu Ser Pro
    130                 135                 140

Gly Cys
145

<210> SEQ ID NO 9
<211> LENGTH: 438
<212> TYPE: DNA
<213> ORGANISM: Artificial Sequence
<220> FEATURE:
<223> OTHER INFORMATION: Synthetic

<400> SEQUENCE: 9
gtgcccatcc aaaaagtcca agatgacacc aaaaccctca tcaagacaat tgtcaccagg      60
atcaatgaca tttcacacac gcagtcagtc tcctccaaac agaaagtcac tggtgcggct     120
ttcattcctg gctccacccc atcctgacct tatccaaga tggaccagac actggcagtc      180
taccaacaga tcctcaccag tatgccttcc agaaacgtga tccgaatatc caacgacctg     240
gagaacctcc gggatcttct tcacgtgctg gccttctcta agagctgcca cttgccctgg     300
gccagtggcc tggagacctt ggacagcctg ggggtgtcc tggaagcttc aggctactcc     360
acagaggtgg tggccctgag caggctgcag gggtctctgc aggacatgct gtggcagctg    420
gacctcagcc ctgggtgc                                                  438

<210> SEQ ID NO 10
<211> LENGTH: 438
<212> TYPE: DNA
<213> ORGANISM: Artificial Sequence
<220> FEATURE:
<223> OTHER INFORMATION: Synthetic

<400> SEQUENCE: 10
gtgcccatcc aaaaagtcca agatgacacc aaaaccctca tcaagacaat tgtcaccagg      60
atcaatgaca tttcacacac gcagtcagtc tcctccaaac agaaagtcac tggtttggac     120
gccgctcctg gctccacccc atcctgacct tatccaaga tggaccagac actggcagtc      180
taccaacaga tcctcaccag tatgccttcc agaaacgtga tccgaatatc caacgacctg     240
gagaacctcc gggatcttct tcacgtgctg gccttctcta agagctgcca cttgccctgg     300
gccagtggcc tggagacctt ggacagcctg ggggtgtcc tggaagcttc aggctactcc     360
acagaggtgg tggccctgag caggctgcag gggtctctgc aggacatgct gtggcagctg    420
gacctcagcc ctgggtgc                                                  438

<210> SEQ ID NO 11
<211> LENGTH: 438
<212> TYPE: DNA
<213> ORGANISM: Artificial Sequence
<220> FEATURE:
<223> OTHER INFORMATION: Synthetic

<400> SEQUENCE: 11

```
gtgtcgatcc gcaaggtcca ggatgacacc aaaaccctca tcaagacgat tgtcaccagg      60
atcaatgaca tctcacacac gcagtccgtc tcctccaaac agagggtcac cggtgctgct     120
ttcatccctg gctccaccc tctcctgagt ttgtccaaga tggaccagac attggcaatc     180
taccaacaga tcctcgccag tctgccttcc agaaatgtga tccaaatatc taatgacctg     240
gagaacctcc gggaccttct ccacctgctg gccgcctcca agagctgccc cttgccgcag     300
gtcagggccc tagagagctt ggagagcctg ggcgtcgtcc tggaagcctc cctctactcc     360
accgaggtgg tggccctgag ccggctacag gggtctctac aggacatgtt gcggcagctg     420
gacctgagtc ccggctgc                                                    438
```

<210> SEQ ID NO 12
<211> LENGTH: 438
<212> TYPE: DNA
<213> ORGANISM: Artificial Sequence
<220> FEATURE:
<223> OTHER INFORMATION: Synthetic

<400> SEQUENCE: 12

```
gtgtcgatcc gcaaggtcca ggatgacacc aaaaccctca tcaagacgat tgtcaccagg      60
atcaatgaca tctcacacac gcagtccgtc tcctccaaac agagggtcac cggtttggac     120
gctgctcctg gctccaccc tctcctgagt ttgtccaaga tggaccagac attggcaatc     180
taccaacaga tcctcgccag tctgccttcc agaaatgtga tccaaatatc taatgacctg     240
gagaacctcc gggaccttct ccacctgctg gccgcctcca agagctgccc cttgccgcag     300
gtcagggccc tagagagctt ggagagcctg ggcgtcgtcc tggaagcctc cctctactcc     360
accgaggtgg tggccctgag ccggctacag gggtctctac aggacatgtt gcggcagctg     420
gacctgagtc ccggctgc                                                    438
```

<210> SEQ ID NO 13
<211> LENGTH: 438
<212> TYPE: DNA
<213> ORGANISM: Artificial Sequence
<220> FEATURE:
<223> OTHER INFORMATION: Synthetic

<400> SEQUENCE: 13

```
gtgcccatcc aaaagtcca agatgacacc aaaaccctca tcaagacaat tgtcaccagg      60
atcaatgaca tttcacacac gcagtcagtc tcctccaaac agaaagtcac tggtgcggct     120
gccattcctg gctccaccc catcctgacc ttatccaaga tggaccagac actggcagtc     180
taccaacaga tcctcaccag tatgccttcc agaaacgtga tccgaatatc caacgacctg     240
gagaacctcc gggatcttct tcacgtgctg gccttctcta agagctgcca cttgccctgg     300
gccagtggcc tggagacctt ggacagcctg ggggtgtcc tggaagcttc aggctactcc     360
acagaggtgg tggccctgag caggctgcag gggtctctgc aggacatgct gtggcagctg     420
gacctcagcc ctgggtgc                                                    438
```

-continued

<210> SEQ ID NO 14
<211> LENGTH: 438
<212> TYPE: DNA
<213> ORGANISM: Artificial Sequence
<220> FEATURE:
<223> OTHER INFORMATION: Synthetic

<400> SEQUENCE: 14

| gtgtcgatcc gcaaggtcca ggatgacacc aaaaccctca tcaagacgat tgtcaccagg | 60 |
| atcaatgaca tctcacacac gcagtccgtc tcctccaaac agagggtcac cggtgctgca | 120 |
| gctatccctg gctccaccc tctcctgagt ttgtccaaga tggaccagac attggcaatc | 180 |
| taccaacaga tcctcgccag tctgccttcc agaaatgtga tccaaatatc taatgacctg | 240 |
| gagaacctcc gggaccttct ccacctgctg gccgcctcca gagctgccc cttgccgcag | 300 |
| gtcagggccc tagagagctt ggagagcctg ggcgtcgtcc tggaagcctc cctctactcc | 360 |
| accgaggtgg tggccctgag ccggctacag gggtctctac aggacatgtt gcggcagctg | 420 |
| gacctgagtc ccggctgc | 438 |

<210> SEQ ID NO 15
<211> LENGTH: 438
<212> TYPE: DNA
<213> ORGANISM: Artificial Sequence
<220> FEATURE:
<223> OTHER INFORMATION: Synthetic

<400> SEQUENCE: 15

| gtgcccatcc aaaaagtcca agatgacacc aaaaccctca tcaagacaat tgtcaccagg | 60 |
| atcaatgaca tttcacacac gcagtcagtc tcctccaaac agaaagtcac tggtgcggct | 120 |
| gccgctcctg gctccaccc catcctgacc ttatccaaga tggaccagac actggcagtc | 180 |
| taccaacaga tcctcaccag tatgccttcc agaaacgtga tccgaatatc caacgacctg | 240 |
| gagaacctcc gggatcttct tcacgtgctg gccttctcta gagctgcca cttgccctgg | 300 |
| gccagtggcc tggagacctt ggacagcctg ggggtgtcc tggaagcttc aggctactcc | 360 |
| acagaggtgg tggccctgag caggctgcag gggtctctgc aggacatgct gtggcagctg | 420 |
| gacctcagcc ctgggtgc | 438 |

<210> SEQ ID NO 16
<211> LENGTH: 438
<212> TYPE: DNA
<213> ORGANISM: Artificial Sequence
<220> FEATURE:
<223> OTHER INFORMATION: Synthetic

<400> SEQUENCE: 16

| gtgtcgatcc gcaaggtcca ggatgacacc aaaaccctca tcaagacgat tgtcaccagg | 60 |
| atcaatgaca tctcacacac gcagtccgtc tcctccaaac agagggtcac cggtgctgct | 120 |
| gctgctcctg gctccaccc tctcctgagt ttgtccaaga tggaccagac attggcaatc | 180 |
| taccaacaga tcctcgccag tctgccttcc agaaatgtga tccaaatatc taatgacctg | 240 |
| gagaacctcc gggaccttct ccacctgctg gccgcctcca gagctgccc cttgccgcag | 300 |
| gtcagggccc tagagagctt ggagagcctg ggcgtcgtcc tggaagcctc cctctactcc | 360 |
| accgaggtgg tggccctgag ccggctacag gggtctctac aggacatgtt gcggcagctg | 420 |
| gacctgagtc ccggctgc | 438 |

<210> SEQ ID NO 17
<211> LENGTH: 41
<212> TYPE: DNA
<213> ORGANISM: Artificial Sequence
<220> FEATURE:
<223> OTHER INFORMATION: Synthetic

<400> SEQUENCE: 17
ccaaacagaa agtcactggt gcggctttca ttcctgggct c         41

<210> SEQ ID NO 18
<211> LENGTH: 41
<212> TYPE: DNA
<213> ORGANISM: Artificial Sequence
<220> FEATURE:
<223> OTHER INFORMATION: Synthetic

<400> SEQUENCE: 18
gagcccagga atgaaagccg caccagtgac tttctgtttg g         41

<210> SEQ ID NO 19
<211> LENGTH: 45
<212> TYPE: DNA
<213> ORGANISM: Artificial Sequence
<220> FEATURE:
<223> OTHER INFORMATION: Synthetic

<400> SEQUENCE: 19
ccaaacagaa agtcactggt ttggacgccg ctcctgggct ccacc     45

<210> SEQ ID NO 20
<211> LENGTH: 45
<212> TYPE: DNA
<213> ORGANISM: Artificial Sequence
<220> FEATURE:
<223> OTHER INFORMATION: Synthetic

<400> SEQUENCE: 20
ggtggagccc aggagcggcg tccaaaccag tgactttctg tttgg     45

<210> SEQ ID NO 21
<211> LENGTH: 41
<212> TYPE: DNA
<213> ORGANISM: Artificial Sequence
<220> FEATURE:
<223> OTHER INFORMATION: Synthetic

<400> SEQUENCE: 21
ccaaacagaa agtcactggt gcggccgcca ttcctgggct c         41

<210> SEQ ID NO 22
<211> LENGTH: 41
<212> TYPE: DNA
<213> ORGANISM: Artificial Sequence
<220> FEATURE:
<223> OTHER INFORMATION: Synthetic

<400> SEQUENCE: 22
gagcccagga atggcggccg caccagtgac tttctgtttg g         41

<210> SEQ ID NO 23
<211> LENGTH: 45
<212> TYPE: DNA
<213> ORGANISM: Artificial Sequence
<220> FEATURE:
<223> OTHER INFORMATION: Synthetic

```
<400> SEQUENCE: 23
ccaaacagaa agtcactggt gcggccgccg ctcctgggct ccacc          45

<210> SEQ ID NO 24
<211> LENGTH: 45
<212> TYPE: DNA
<213> ORGANISM: Artificial Sequence
<220> FEATURE:
<223> OTHER INFORMATION: Synthetic

<400> SEQUENCE: 24
ggtggagccc aggagcggcg gccgcaccag tgactttctg tttgg          45

<210> SEQ ID NO 25
<211> LENGTH: 41
<212> TYPE: DNA
<213> ORGANISM: Artificial Sequence
<220> FEATURE:
<223> OTHER INFORMATION: Synthetic

<400> SEQUENCE: 25
cagagggtca ccggtgctgc tttcatccct gggctccacc c              41

<210> SEQ ID NO 26
<211> LENGTH: 41
<212> TYPE: DNA
<213> ORGANISM: Artificial Sequence
<220> FEATURE:
<223> OTHER INFORMATION: Synthetic

<400> SEQUENCE: 26
gggtggagcc cagggatgaa agcagcaccg gtgaccctct g              41

<210> SEQ ID NO 27
<211> LENGTH: 44
<212> TYPE: DNA
<213> ORGANISM: Artificial Sequence
<220> FEATURE:
<223> OTHER INFORMATION: Synthetic

<400> SEQUENCE: 27
cctccaaaca gagggtcacc ggtttggacg ctgctcctgg gctc           44

<210> SEQ ID NO 28
<211> LENGTH: 44
<212> TYPE: DNA
<213> ORGANISM: Artificial Sequence
<220> FEATURE:
<223> OTHER INFORMATION: Synthetic

<400> SEQUENCE: 28
gagcccagga gcagcgtcca aaccggtgac cctctgtttg gagg           44

<210> SEQ ID NO 29
<211> LENGTH: 46
<212> TYPE: DNA
<213> ORGANISM: Artificial Sequence
<220> FEATURE:
<223> OTHER INFORMATION: Synthetic

<400> SEQUENCE: 29
tccaaacaga gggtcaccgg tgctgcagct atccctgggc tccacc         46

<210> SEQ ID NO 30
<211> LENGTH: 46
```

```
<212> TYPE: DNA
<213> ORGANISM: Artificial Sequence
<220> FEATURE:
<223> OTHER INFORMATION: Synthetic

<400> SEQUENCE: 30
gggtggagcc cagggatagc tgcagcaccg gtgaccctct gtttgg            46

<210> SEQ ID NO 31
<211> LENGTH: 40
<212> TYPE: DNA
<213> ORGANISM: Artificial Sequence
<220> FEATURE:
<223> OTHER INFORMATION: Synthetic

<400> SEQUENCE: 31
cagagggtca ccggtgctgc tgctgctccc gggctccacc                   40

<210> SEQ ID NO 32
<211> LENGTH: 41
<212> TYPE: DNA
<213> ORGANISM: Artificial Sequence
<220> FEATURE:
<223> OTHER INFORMATION: Synthetic

<400> SEQUENCE: 32
gggtggagcc cgggagcagc agcagcaccg gtgaccctct g                 41
```

LEPTIN ANTAGONISTS

FIELD OF THE INVENTION

The present invention relates to leptin antagonists and, in particular, to leptin mutants, and to pharmaceutical compositions comprising them.

BACKGROUND OF THE INVENTION

The product of the ob gene, leptin, was reported to suppress appetite by regulating activities of the satiety centers in the brain via its receptor, termed OB-R, and to affect body weight (Friedman and Halaas, 1998). However, further studies have shown that leptin receptors are expressed in many other tissues (Cioffi et al., 1996; Emilsson et al., 1997; Hoggard et al., 1997; Glasow et al., 1998; Briscoe et al., 2001), and have suggested that leptin is involved in more diverse biological functions than expected previously.

Systematic investigations have demonstrated that serum levels of leptin are increased in obese humans as they are in various animal models of obesity (Dagogo-Jack et al., 1996). It has been reported that the OB polypeptide or "leptin" lowers both plasma insulin and glucose levels in the genetically obese ob/ob mouse (Pelleymounter et al., 1995). There has so far been no indication that mutations in the ob gene might be responsible for the frequent occurrence of obesity in humans.

U.S. Pat. No. 6,309,853 discloses OB polypeptides and fragments thereof, and their use for modulating body weight.

Non-insulin-dependent diabetes (NIDDM) or type II diabetes is caused by insulin resistance, particularly in skeletal muscle, adipose tissue and liver. Thus, despite hyperinsulinaemia, there is insufficient insulin to compensate for the insulin resistance and to maintain blood glucose in the desirable range. U.S. Pat. No. 6,399,745 discloses the use of leptin antagonists, which are fragments of human or murine leptin, for treating type II diabetes and insulin resistance in diabetic patients. US Patent Application No. 2004/0048773 discloses the use of an antagonist of leptin for treatment of disorders resulting from deficiencies in insulin secretion and of hyperglycaemia, but no specific leptin antagonist is disclosed in this application.

US Patent Application No. 2004/0072219 discloses a modified molecule having the biological activity of human leptin and being substantially non-immunogenic or less immunogenic than any non-modified molecule having the same biological activity when used in vivo. The variant leptin proteins disclosed have been designed by computer modeling, but have not been synthesized nor tested. These variants have altered T-cell epitopes, preferably by substitution of one sole amino acid, to reduce or remove immunogenic sites, while maintaining the leptin biological activity. Among the sequences disclosed are 13-mers in which the amino acid residue 39, 41 or 42 of native human leptin has been substituted with alanine.

Obesity is considered a risk for many cancers. Serum leptin levels are often elevated in obese people. Leptin acts as a mitogenic agent in many tissues; therefore, it may act to promote cancer cell growth. In fact, leptin was shown to act as a growth factor for prostate cancer cells in vitro, to induce increased migration of prostate cancer cells and expression of growth factors such as vascular endothelial growth factor (VEGF), transforming growth factor-betal (TGF-β1), and basic fibroblast growth factor (bFGF), and to enhance prostate cancer growth. (Somasundar et al., 2004; Frankenberry et al., 2004).

Besides playing an important role in the regulation of food intake and energy consumption in the brain, leptin also acts as a potential growth stimulator in normal and neoplastic breast cancer cells. It was also shown recently to induce cell proliferation in ovarian cancer cells in vitro (Choi et al., 2004).

SUMMARY OF THE INVENTION

We have now found, according to the present invention, that by reducing the hydrophobicity of a mammal leptin-binding site at positions 39-42, leptin mutants are obtained that are leptin antagonists.

Thus, in one aspect, the present invention provides a synthetic leptin antagonist in which at least two amino acid residues of the sequence LDFI (SEQ ID NO:33) of the hydrophobic binding site at positions 39-42 of a native leptin polypeptide sequence are substituted by different amino acid residues such that the site becomes less hydrophobic, and fragments of said leptin antagonist.

In another aspect, the present invention provides an isolated DNA molecule encoding said leptin antagonist.

In a further aspect, the present invention provides a pharmaceutical composition comprising said synthetic leptin antagonist, or a fragment thereof, and a pharmaceutically acceptable carrier.

BRIEF DESCRIPTION OF THE FIGURES

FIGS. 1A-1C show purity determination of the isolated human and ovine leptin mutants. (A) Gel-filtration analysis, (B) SDS-PAGE analysis (15% gel), lanes 1-5 correspond to human wild-type (WT) leptin, L39A/D40A, F41A/I42A, L39A/D40A/F41A and L39A/D40A/F41A/I42A leptin mutants and lanes 6-10 to corresponding WT ovine leptin and its mutants, and (C) reverse phase chromatography.

FIG. 2 shows gel-filtration analysis of complex between chicken leptin binding domain (chLBD) and human or ovine leptin on a Superdex™ 75 HR 10/30 column. Complex formation was carried out during a 20-min incubation at room temperature in TN buffer using various molar ratios and then aliquots (200 μl) of the mixture were applied to the column, pre-equilibrated with the same buffer. The initial leptin concentration (10 μM) was constant in all cases. The column was developed at 0.8 ml/min and calibrated with bovine serum albumin (66 kDa), ovine placental lactogen (23 kDa) and lysozyme (14 kDa). Protein concentration in the eluate was monitored by absorbance at 220 nm.

FIGS. 3A-3B show radioreceptor assay (RRA) using homogenate of BAF3 cells stably transfected with the long form of human leptin receptor. $^{125}$I-ovine leptin was used as a ligand and human (A) or ovine (B) leptins or their analogues as competitors.

FIGS. 4A-4B show inhibition of leptin acitivity by human leptin L39A/D40A/F41A/I42A mutant. (A) Inhibition of leptin-induced phosphorylation of MAPK (erk1/2) in SH-SY5Y human neuroblastoma cells bioassay (the upper figure shows effect of increased leptin dose) and (B) inhibition of leptin-inducible transactivation of luciferase reporting gene in CHO cells transiently transfected with leptin receptor and stimulated with 6.25 nM of human leptin.

FIG. 5 shows Hydrophobic Cluster Analysis (HCA). The analysis was done assuming the leptin site III interaction with immunoglobulin-like domain (IGD) of leptin receptor (LEPR) resembles that of IL-6 interacting with gp130. The highlighted hydrophobic clusters mainly correspond to the regular secondary structures of the considered protein as shown in FIG. 6.

Figure 6:

FIG. 6 shows comparative 3D models of viral IL-6 (vIL-6) interacting with the IGD domain of gp130 (upper) and corresponding human leptin (lower): Site III—Comparison of the experimental structure of viral IL-6, as observed in complex with gp130 (top—only the D1 domain of one gp130 molecule is shown in gray in the ribbon representation shown at left) and isolated human leptin, for which no residues were visible in the electronic density for the disordered AB loop (bottom—orange dotted line). The two structures were superimposed on the basis of the structurally conserved helices (rmsd 2.2 superimposition on 89 C±atoms). Tyr119 of leptin was shown in violet in the figure at bottom.

DETAILED DESCRIPTION OF THE INVENTION

The leptin tertiary structure solution revealed its pertinence to the long-chain cytokine superfamily (Zhang et al., 1997). Although the tertiary structure of the leptin receptor has been determined, yet its amino acid sequence analysis indicated the high similarity to receptors of the class I cytokine receptor family, like receptors for growth hormone (GH), granulocyte colony-stimulating factor (G-CSF), interleukin-6 (IL-6) and erythropoietin (EPO). The receptors from this family share multiple similar domains in their extra cellular part, like C2, CK and F3. Like the G-CSFR, leptin receptor has two repeats of CK-F3 domains, which suggested being the ligand binding site (Wells and de Vos, 1996; Livnah et al., 1999; Aritomi et al., 1999). Fong and co-workers localized the leptin binding domain (LBD) to the membrane-proximal CK-F3 domain (~200 amino acids) in the leptin receptor extracellular domain (ECD) (Fong et al. 1999). However, recent data show that the binding of leptin to its receptor resembles more the interaction of IL-6 with its receptor (Boulanger et al, 2003; Muller-Newen 2003) and the immunoglobulin-like domain (IGD) located between the distal and the proximal CK-F3 is essential for productive dimerization of the leptin receptor (Zabeau et al. 2004).

As no structural information of the 3D structure of leptin receptor exists, two possible models may be considered. One, characteristic for GH/GHR, or for prolactin (PRL)/PRLR or EPO/EPOR, which is characterized by hormone induced receptor homodimerization that brings the juxtaposed Jak2 to mutual transphosphorylation (De Vos et al., 1992), and another suggested for IL-6 (Muller-Newen, 2003). In the later model, a hexameric complex is formed gradually, first by IL-6 molecule, which interacts with the IL-6R-alpha, then with gp130forming an inactive trimer, which subsequently dimerizes forming an active hexamer. Formation of the hexamer is achieved due to interaction of IL-6 bound in one trimer (through its site III) with IGD of gp130 of the other trimer (Boulanger et al., 2003; Muller-Newen, 2003). To evaluate the possible interaction site of putative leptin's binding site III and IGD, we modeled the leptin receptor on the basis of its alignment with gp130, whose 3D structure is available. Subsequently, leptin was fitted on vIL-6 of the IL-6/gp130 complex (based on the superimposition of four conserved blocks) and the leptin receptor IGD was fitted on gp130 IGD. Despite the missing information on the AB loop, we have identified the leptin's amino acids 39-42 (LDFI (SEQ ID No:33) in most mammals, which are preserved in all leptin species as a main putative sequence that interacts with IGD. To verify this hypothesis and to test its generality, we have prepared and purified to homogeneity 4 ovine and 4 human recombinant leptin alanine mutants of this region and show herein that they act as competitive antagonists.

The present invention thus provides a synthetic leptin antagonist in which at least two amino acid residues of the sequence LDFI (SEQ ID NO:33) of the hydrophobic binding site at positions 39-42 of a native mammal leptin polypeptide sequence are substituted with different amino acid residues such that the site becomes less hydrophobic, and fragments of said leptin antagonist.

As used herein, the term "mammal" includes human mammal as well as non-human mammals. Thus, according to the present invention, the native leptin may be human leptin or a non-human mammal leptin such as, but not limited to, ovine, rat, mouse, and pig leptin, and the LDFI (SEQ ID NO:33) sequences represent the 39-42 LDFI (SEQ ID NO:33) sequence of human leptin or of a non-human mammal leptin. In one preferred embodiment, the leptin is human leptin. In another preferred embodiment, the leptin is ovine leptin.

As used herein, the terms "leptin antagonist" and "leptin mutant" are used interchangeably to denote a mammal leptin polypeptide in which at least two of the amino acids at positions 39-42 of a wild-type human or non-human mammal leptin sequence are substituted with other amino acids such that the site becomes less hydrophobic. The term "mammal leptin polypeptide" encompasses naturally occurring mammal leptin polypeptides and biologically active variants thereof, as well as biologically active fragments of naturally occurring leptin and variants thereof. "Variant" refers to a polypeptide differing from the mammal leptin polypeptide, but retaining essential properties thereof.

According to the present invention, at least two of the amino acid residues at positions 39-42 of a wild-type mammal leptin may be substituted with one or more amino acid residues selected from the group consisting of alanine, arginine, aspartatic acid, glutamic acid, glycine, lysine and serine. In a most preferred embodiment, said amino acid residue is alanine.

In a preferred embodiment of the invention, any two of the amino acid residues at any of the positions 39-42 of a mammal leptin polypeptide sequence are substituted by alanine, for example at positions 39, 40, or 39, 41, or 39, 42, or 40, 41, or 40, 42, or 41, 42.

In one embodiment, the leptin antagonist with two alanine substitutions is derived from human leptin. In a preferred embodiment, the human leptin antagonist is the human recombinant leptin polypeptide that carries two Ala mutations at positions 39 and 40, herein designated human leptin L39A/D40A mutant (SEQ ID NO: 1). In another preferred embodiment, the human leptin antagonist is the human recombinant leptin polypeptide that carries two Ala mutations at positions 41 and 42, herein designated human leptin F41A/I42A mutant (SEQ ID NO: 2).

In another embodiment of the invention, the leptin antagonist with two alanine substitutions is derived from ovine leptin. In a preferred embodiment, the ovine leptin antagonist is the ovine recombinant leptin polypeptide that carries two Ala mutations at positions 39 and 40, herein designated ovine leptin L39A/D40A mutant (SEQ ID NO: 3). In another preferred embodiment, the leptin antagonist is the ovine recombinant leptin polypeptide that carries two Ala mutations at positions 41 and 42, herein designated ovine leptin F41A/I42A mutant (SEQ ID NO: 4).

In another preferred embodiment of the invention, any three of the amino acid residues at any of the positions 39-42 of a leptin polypeptide sequence are substituted by alanine, for example at positions 39, 40, 41 or 39, 40, 42, or 39, 41, 42, or 40, 41, 42.

In one preferred embodiment of the invention, the leptin antagonist with three alanine substitutions is derived from human leptin. In a more preferred embodiment, the human leptin antagonist is the human recombinant leptin polypeptide that carries three Ala mutations at positions 39, 40 and 41, herein designated human leptin L39A/D40A/F41A mutant (SEQ ID NO: 5).

In another preferred embodiment of the invention, the leptin antagonist with three alanine substitutions is derived from ovine leptin. In a more preferred embodiment, the ovine leptin antagonist is the ovine recombinant leptin polypeptide that carries three Ala mutations at positions 39, 40, and 41, herein designated ovine leptin L39A/D40A/F41A mutant (SEQ ID NO: 6).

In another preferred embodiment of the invention, the four amino acid residues at positions 39-42 of a leptin polypeptide sequence are substituted by alanine. In one more preferred embodiment, the leptin antagonist with the four alanine substitutions is derived from human leptin and is the human recombinant leptin polypeptide that carries four Ala mutations at positions 39, 40, 41 and 42, herein designated human leptin L39A/D40A/F41A/I42A mutant (SEQ ID NO: 7). In another more preferred embodiment, the leptin antagonist with the four alanine substitutions is derived from ovine leptin and is the ovine recombinant leptin polypeptide that carries four Ala mutations at positions 39, 40, 41 and 42, herein designated L39A/D40A/F41A/I42A (SEQ ID NO: 8).

In another aspect, the present invention relates to an isolated DNA molecule encoding a leptin antagonist of the invention.

In one preferred embodiment, the isolated DNA molecule encodes a leptin antagonist derived from human leptin. In one preferred embodiment, the DNA molecule is of SEQ ID NO: 9 and encodes the double human leptin mutant L39A/D40A. In another embodiment, the DNA molecule is of SEQ ID NO: 10 and encodes the double human leptin mutant F41A/I42A.

In another embodiment, the isolated DNA molecule encodes a leptin antagonist derived from ovine leptin. In one preferred embodiment, the DNA molecule is of SEQ ID NO: 11 and encodes the double mutant L39A/D40A of ovine leptin. In another preferred, the DNA molecule is of SEQ ID NO: 12 and encodes the double mutant F41A/I42A of ovine leptin.

In a more preferred embodiment of the invention, the DNA molecule is of SEQ ID NO: 13 and encodes the triple mutant L39A/D40A/F41A of human leptin. In another more preferred embodiment, the DNA molecule is of SEQ ID NO: 14 and encodes the triple mutant L39A/D40A/F41A of ovine leptin.

In another more preferred embodiment, the DNA molecule is of SEQ ID NO: 15 and encodes the quadruple mutant L39A/D40A/F41A/I42A of human leptin.

In a further more preferred embodiment, the DNA molecule is of SEQ ID NO: 16 and encodes the quadruple mutant L39A/D40A/F41A/I42A of ovine leptin.

For the preparation of the leptin mutants of the invention, site directed mutagenesis of the ob gene is carried out by procedures well known in the art, for example using commercially available kits. The mutants are screened, sequenced to confirm the correct mutation, the mutated plasmids are isolated, and competent cells are transformed with the plasmids and used for expression of the leptin mutants.

In another embodiment, the present invention relates to a synthetic leptin antagonist fragment, said fragment comprising a mutated site at positions 39-42, as described for the full-length leptin polypeptide antagonist, and wherein said fragment is itself a leptin antagonist.

In a further embodiment, the synthetic leptin antagonist of invention is in pegylated form and has a variable number of polyethylene glycol (PEG) molecules attached thereto. PEG of molecular weight of 4,000-6,000 D is suitable for this purpose. The pegylation of the leptin antagonists of the invention increases their stability, their plasma half-life and pharmacokinetics.

In another aspect, the present invention provides a pharmaceutical composition comprising a synthetic leptin antagonist of the invention and a pharmaceutically acceptable carrier. The pharmaceutical composition of the invention is useful in treating any disorder in which a non-desirable or deleterious activity of endogenous leptin is implicated, as for example in type II diabetes, anorexia and cancer.

Thus, in a preferred embodiment, the invention provides a pharmaceutical composition for treatment of type II diabetes and for the treatment of insulin resistance, especially that associated with obesity in a human or non-human mammal.

In another preferred embodiment, the pharmaceutical composition can be used for inhibition of malignant cell growth and can thus be useful in the treatment of cancer such as, but not limited to, breast, colon, ovarian and prostate cancer.

Pharmaceutical compositions for use in accordance with the present invention may be formulated in conventional manner using one or more physiologically acceptable carriers or excipients. The carrier(s) must be "acceptable" in the sense of being compatible with the other ingredients of the composition and not deleterious to the recipient thereof.

Methods of administration of the pharmaceutical compositions of the invention include, but are not limited to, parenteral, e.g., intravenous, intraperitoneal, intramuscular, subcutaneous, mucosal (e.g., oral, intranasal, buccal, vaginal, rectal, intraocular), intrathecal, topical and intradermal routes. Administration can be systemic or local.

In another aspect, the present invention relates to a method for treatment of type II diabetes which comprises administering to a diabetic patient an effective amount of a leptin antagonist of the invention, or a fragment thereof.

In a further aspect, the present invention relates to a method for treatment of cancer which comprises administering to a cancer patient an effective amount of a leptin antagonist of the invention, or a fragment thereof.

Besides their potential pharmaceutical use, the leptin antagonists of the invention are useful as research tools for study of the biological activities of the leptin hormone.

The invention will now be illustrated by the following non-limiting examples.

EXAMPLES

Materials and Methods (i) Materials. Ovine and human leptins were prepared in our laboratory as described previously (Getler et al. 1998, Raver et al. 2002). Recombinant chicken leptin binding domain (chLBD) was prepared similarly to the preparation of human LBD (Sandowski et al 2002, Raver et al 2003). Restriction enzymes used in the molecular biology experiments were from Fermentas (Vilnius, Lithuania) and New England Biolabs (Beverly, Mass.). Highly pure DNA primers were ordered from Sigma Co. (Rehovot Israel). RPMI-1640 medium, interleukin-3 (IL-3), nalidixic acid and 3-(4,5-dimethylthiazol-2-yl) -2,5-diphenyltetrazolium bromide (thiazolyl blue, MTT) were purchased from Sigma Chemical Co. (St. Louis, Mo.), fetal calf serum (FCS) from Biolab Co. (Jerusalem, Israel) and pTrc 99A expression vector, Superdex75 HR 10/30 column, Q-Sepharose from Pharmacia LKB Biotechnology AB (Uppsala, Sweden). A research-grade CM5 sensor chip, N-hydroxysuccinimide (NHS), N-ethyl-N' (3-dimethylaminopropyl)-carbodiimide hydrochloride (EDO), ethanolamine-HCl and HBS-EP running buffer (10 mM Hepes, 150 mM NaCl, 3.4 mM EDTA and 0.005% (v/v) surfactant P20 at pH 7.4) were purchased from Biacore, AB (Uppsala, Sweden). All other chemicals were of analytical grade.

(ii) Determination of purity and monomer content. SDS-PAGE was carried out according to Laemmli (Laemmli, 1970) in a 15% polyacrylamide gel under reducing conditions. Gel was stained with Coomassie Brilliant Blue R. Gel-filtration chromatography was performed on a Superdex™ 75. HR 10/30 column with 0.2-ml aliquots of the Q Sepharose column-eluted fraction using TN buffer (25 mM Tris-HCl, 150 mM NaCl, pH 8). Reverse phase chromatography was carried-out using Vydax column developed with a gradient of 0.1% TFA in water (solvent A) and 0.1% TFA in MeCN (solvent B).

(iii) Determination of CD spectra. The CD spectra in millidegrees were measured with an AVIV model 62A DS circular dichroism spectrometer (Lakewood, N.J.) using a 0.020-cm rectangular QS Hellma cuvette. The spectrometer was calibrated with camphorsulfonic acid. The absorbtion spectra were measured with an AVIV model 17DS UV-visible IR spectrophotometer using a 1.000-cm QS cuvette and correction for light scattering. Q Sepharose-eluted concentrated chLBD was dialyzed against 20 mM phosphate buffer, pH 7.5, for 24 h, and then centrifuged at 11,000 g for 15 min. The CD measurements were performed at 25.0° C. as controlled by thermoelectric Peltier elements to an accuracy of 0.1° C. The CD spectra were measured at five repetitions resulting in an average spectrum. Standard deviation of the average CD signal at 222 nm was in the 5% range. For the secondary structure determination, the CD data were expressed in degree $cm^2$/dmol per mean residue, based on a respective molecular mass of ~16 kDa calculated for the protein from the 147 amino acids, as it is known that the N-terminal Met-Ala bond is hydrolyzed in the course of expression (unpublished data). The secondary structure of leptin and leptin mutants was calculated by applying the procedure and computer program CONTIN (Provencher and Glockner, 1981). The program determines α-helices, β-strands and β-turns as a percentage of amino acid residues involved in these ordered forms. Unordered conformation was determined as unity minus the sum of all elements of the secondary structure (Venyaminov and Yang, 1996). In this study, for calculation by the CONTIN program, a set of standard CD spectra of 17 proteins was employed (Sreerama and Woody, 1993).

(iv) Determination of complex stoichiometry. Complexes between chLBD and human or ovine leptins or their mutants were prepared at various molar concentrations in TN buffer. The proteins final concentrations in the 1:1 ratio were 10 μM. After 20-min incubation at room temperature, 200-μl aliquots were applied to a Superdex™ 75 HR 10/30 column prequilibrated with TN buffer. To determine the molecular weight of the complex, the column was calibrated with several pure proteins.

(v) Kinetic measurements of leptin and leptin mutants interaction with chLBD. All experiments were performed at 25° C. using surface plasmon resonance (SPR) methodology. The kinetics and equilibrium constants for the interactions between human and chicken recombinant LBD and chicken and hLep were determined using the Biacore 3000 system (Uppsala, Sweden). Leptin (human, ovine or chicken) was immobilized in a flow cell of a research-grade CM5 (carboxymethyldextran) sensor chip using amine-coupling chemistry (Johnsson et al., 1991). The immobilization steps were carried out at a flow rate of 5 μl/min in HBS-EB buffer. The surface was activated for 7 min with a mixture of 0.05 M N-hydroxysuccinimide and 0.2 M N-ethyl-N'(3-dimetylaminopropyl)-carbodiimide hydrochloride. Leptin was injected at a concentration of 50 μg/ml in 10 mM acetate, pH 3.5, until the desired level (1000 resonance units) was achieved. 1 M ethanolamine, pH 8.5, was injected for 7 min to block the remaining activated groups. A control surface was prepared by activating the carboxyl groups and then blocking the activated groups by ethanolamine as described. For the binding studies, chLBD, resuspended in HBS-EP buffer, was passed at different concentrations (15, 62, 31.25, 62.5, 125 and 250 nM) through 3 flow cells (carrying human or ovine leptin or control) at a rate of 30 μl/min. Regeneration of the surface after each interaction was performed by using 10-μl pulse of 10 mM glycine buffer, pH 2. The experiments were controlled by the kinetics Wizard of the Biacore control software, which corrects automatically for refractive index changes and non-specific binding by subtraction of the responses obtained for the control surface from the data obtained for the interactions between LBD and leptin. The obtained binding curves were fitted to the association and dissociation phases at all LBD concentrations simultaneously using Biacore evaluation software. In all cases, the best fit was obtained for a simple bimolecular interaction (Langmuir model).

(vi) Binding assays. Radiolabeled ovine $^{125}$I-leptin served as a ligand and all other nonlabeled leptins or their mutants as competitors. The experiments were conducted with homogenates of BAF/3 cells stably transfected with the long form of human leptin receptor. The cells were cultured in RPMI 1640 supplemented with 5% FCS in the presence of IL-3 to minimize leptin receptors down-regulation until concentration of $10^6$ cells/ml was reached. Then the cells were spun and stored at −70° C. Prior to each experiment the cells were thawed, suspended at $1.75 \times 10^6$ cells/150 μl of reaction buffer (12.5 mM Na barbiturate, pH 8.6 buffer containing 0.1% bovine serum albumin, 7.5 mM EDTA, 150 mM NaCl and 0.1% (w/v) Triton-X100) and homogenized with Polytrone for 30 sec at 10,000 rpm on ice. Each tube contained 150 μl of reaction buffer, 100 μl $^{125}$I-human leptin (700,000-800,000 cpm) and 100 μl of different leptin solutions (providing 0-5000 ng/tube) in reaction buffer and the reaction was started by addition of 150 μl homogenate. The tubes were incubated for 18 h at room temperature. Then the leptin-receptor complex was precipitated by adding 250 μl of 1% (w/v) bovine immunoglobulin and 500 μl of 20% (w/v) polyethylene glycol. The tubes were thoroughly mixed, incubated for 30 mm at 4° C., and centrifuged at 12,000 g for 15 mm at 4° C. Then supernatant was carefully aspirated and the precipitates were counted in a γ counter. Human leptin was iodinated according to a protocol previously described for the iodination of hGH (Gertler et al., 1984)

(vii) BAF/3 proliferation assays. The proliferation rate of leptin-sensitive BAF/3 1442-CI 4 cells transfected with the long form of human leptin receptor was used to estimate self and antagonistic activity of leptin mutants, using the MTT (tetrazolium salt 3-[4,5-dimethylthiazol-2-yl]-2,5-diphenyltetrazolium bromide) method as previously described (Raver et al., 2000). To determine antagonistic activity of leptin mutants, $6.25 \times 10^{-11}$ M of wild type homologous leptin was added to each well containing also different concentrations of mutated leptins. The average absorbance in wells without leptin (negative control) was used as a blank value and subtracted from other absorbance values to yield the corrected absorbance values. The average absorbance in wells with wild-type leptin after subtraction of the negative control was used as a positive control to calculate percent inhibition. The inhibition curves were drawn using Prizma non-linear regression sigmoidal one site inhibition program (Prizma, 2003) and the $IC_{50}$ values were calculated.

(viii) SH-SY5Y human neuroblastoma cells bioassay. SH-SY5Y human neuroblastoma cells were grown in Dulbecco's modified Eagle's medium supplemented with 10% heat inactivated fetal calf serum, 100 units/ml penicillin and 100 μg/ml streptomycin in 5% $CO_2$ atmosphere at 37° C.; differentiation of SH-SY5Y cells was achieved by treatment with retinoic acid (RA). Differentiated cells were used after 15 days of RA treatment to obtain a high percentage of cells that showed a clear morphological differentiation. SH-SY5Y cells were starved in serum-free Dulbecco's modified Eagle's medium for 16 h, and pre-treated for 15 minutes in the presence or absence of various concentrations of leptin antagonists (6.25 to 320 nM) and then stimulated for 10 minutes with human leptin (6.25 nM) After stimulation, cells were harvested by rinsing in ice-cold PBS and scraping into lysis buffer containing 20 mM Tris-HCl (pH 7.5), 137 mM NaCl, 1 mM $MgCl_2$, 1 mM $CaCl_2$, 1% Nonidet-P40, 10% glycerol, Protease inhibitors (0.35 mg/ml PMSF, 2 μg/ml leupeptin, 2 μg/ml aprotinin and 10 mM benzamidine) and phosphatase inhibitors (10 mM sodium fluoride, 1 mM sodium orthovanadate and 20 mM sodium β-glycerophosphate). After lysis in ice for 30 min, insoluble materials were removed by centrifugation (15.000 rpm at 4° C. for 30 min) and protein concentrations of the resulting lysates were determined using a protein assay kit (Pierce, Chemical). Proteins were resolved by SDS-PAGE and transferred onto nitrocellulose membranes (Schleicher & Schuell). Immunoblots were blocked with non fat dry milk and incubated in the presence of anti-Phospho-MAP kinase or anti-Total MAP kinase (ERK 41/42) (from Cell Signaling) followed by an incubation in the presence of with appropriate secondary antibodies coupled to HRP, nitrocellulose membranes were washed and targeted protein were detected using enhanced chemiluminescence reagents (ECL; Amersham Biosciences).

(ix) Determination of biological activity by activating luciferase reporting gene. Chinese hamster ovary (CHO) cells were grown in HAM-F12 medium containing 10% FCS and maintained at 37° C. in a humidified atmosphere gassed with 95% air, 5% $CO_2$. GC3 minimal medium used before hormonal induction experiments was composed of DMEM-F12, supplemented with glutamine, 100 μg/ml penicillin/streptomycin, nonessential amino acids, transferrin and insulin. CHO cells were co-transfected with the pCH110 along with STAT3-responsive pAH32 luciferase and mouse LEPRb encoding plasmids. All transfections were carried out using ExGen 500 (Euromedex, Souffelweyersheim, France) according to the manufacturer's protocol. To test the biological activity, transfected cells were subsequently incubated for 24 h in the presence of different concentrations of human and ovine leptins in presence or absence of respective leptin mutants in GC3 medium. The plates were washed with phosphate-buffered saline, and the enzymatic activity was determined as described previously (Bignon et al. 1993, Sotiropoulus et al. 1996). The results were expressed as fold induction, after the luciferase activity was normalized by correcting for β-galactosidase activity, as explained earlier.

Example 1

Preparation of Leptin Mutants

To prepare the leptin mutants of the invention, the pMon3401 expression plasmids encoding the wild-type (WT) ovine or human leptin were used as starting material. The leptin inserts was modified with the Stratagene QuickChange mutagenesis kit (La Jolla, Calif.) according to manufacturer's instructions, using two complementary primers (Table 1), The primers were designed to contain base changes (marked in bold) to obtain the respective mutations but still conserve the appropriate amino acid sequence, and to modify a specific BshTI restriction site (underlined) for colony screening. The procedure included 12 PCR cycles using Pfu polymerase. The mutated construct was then digested with DpnI restriction enzyme, which is specific to methylated and hemi-methylated DNA (target sequence: 5'-$G^{m6}$ ATC-3'), in order to digest the template and to select for mutations containing synthesized DNA. The plasmids were then transfected into XL1 competent cells. Five colonies of each mutant were screened for mutation, using the specific restriction site designed, and revealed at least 80% efficiency. Two colonies of each mutant were sequenced and confirmed to contain the mutation but no unwanted misincorporation of nucleotides. XL-1 competent cells were transformed with the mutated plasmids and grown in 5-10 ml LB medium and the plasmids were isolated. Mon105 competent cells were then transformed with the plasmids and used for expression.

The primers of SEQ ID NOs. 17-32 used in this experiment for preparation of the DNA molecules encoding the leptin mutants are shown in Table 1. The modified restriction site (underlined) is BshTI(−) for human leptin and BshTI for ovine leptin.

TABLE 1

Primers used for preparation of leptin mutants

| Primer[a] | Primer sequence | SEQ ID NO. |
|---|---|---|
| Human leptin | | |
| L39A/D40A-5 | S 5'-CCAAACAGAAAGTC<u>ACTGGT</u>GCGGCTTTCATTCCTGGGCTC-3' | 17 |
| L39/AD40A-3 | A 5'-GAGCCCAGGAATGAAAGCCGCAC<u>CAGT</u>GACTTTCTGTTTGG-3' | 18 |

TABLE 1-continued

Primers used for preparation of leptin mutants

| Primer[a] | Primer sequence | SEQ ID NO. |
|---|---|---|
| F41A/I42A-5 | S 5'-CCAAACAGAAAGTCACTGGTTTGGACGCCGCTCCTGGGCTCCACC-3' | 19 |
| F41A/I42A-3 | A 5'-GGTGGAGCCCAGGGAGCGGCGTCCAAACCAGTGACTTTCTGTTTGG-3' | 20 |
| L39A/D40A/F41A-5 | S 5'-CCAAACAGAAAGTCACTGGTGCGGCCGCCATTCCTGGGCTC-3' | 21 |
| L39A/D40A/F41A-3 | A 5'-GAGCCCAGGAATGGCGGCCGCACCAGTGACTTTCTGTTTGG-3' | 22 |
| L39A/D40A/F41A/I42A-5 | S 5'-CCAAACAGAAAGTCACTGGTGCGGCCGCCGCTCCTGGGCTCCACC-3' | 23 |
| L39A/D40A/F41A/I42A-3 | A 5'-GGTGGAGCCCAGGAGCGGCGGCCGCACCAGTGACTTTCTGTTTGG-3' | 24 |
| Ovine leptin | | |
| L39A/D40A-5 | S 5'-CAGAGGGTCACCGGTGCTGCTTTCATCCCTGGGCTCCACCC-3' | 25 |
| L39A/D40A-3 | A 5'-GGGTGGAGCCCAGGGATGAAAGCAGCACCGGTGACCCTCTG-3' | 26 |
| F41A/I42A-5 | S 5'-CCTCCAAACAGAGGGTCACCGGTTTGGACGCTGCTCCTGGGCTC-3' | 27 |
| F41A/I42A-3 | A 5'-GAGCCCAGGAGCAGCGTCCAAACCGGTGACCCTCTGTTTGGAGG-3' | 28 |
| L39A/D40AF41A-5 | S 5'-TCCAAACAGAGGGTCACCGGTGCTGCAGCTATCCCTGGGCTCCACCC-3' | 29 |
| L39A/D40AF41A-3 | A 5'-GGGTGGAGCCCAGGGATAGCTGCAGCACCGGTGACCCTCTGTTTGGA-3' | 30 |
| L39A/D40A/F41A/I42A-5 | S 5'-CAGAGGGTCACCGGTGCTGCTGCTGCTCCCGGGCTCCACCC-3' | 31 |
| L39A/D40A/F4A/I42A-3 | A 5'-GGGTGGAGCCCGGGAGCAGCAGCAGCACCGGTGACCCTCTG-3' | 32 |

[a]S, sense primer; A, antisense primer; all mutations are in bold letters.

Example 2

Expression and Refolding of Human and Ovine Leptins and Their Mutants

The recombinant wild-type (WT) or mutated human leptins with an extra methionine-alanine at the N-terminus were expressed upon nalidixic acid induction (50 μg/ml) in 2.5 l culture of MON 105 cells, transformed with the appropriate expression plasmid. Transformed bacteria were first grown in 5×500 ml in 2.5-liter flasks in Terrific Broth (TB) medium at 37° C. to an $A_{600}$ of 0.9 with constant shaking of 200 rpm. Four hours after addition of nalidixic acid the cells were harvested by 10-min centrifugation at 10,000 g and frozen at −20° C. The bacterial pellet from 2.5 l of bacterial culture was thawed on ice and resuspended in lysis buffer (10 mM Tris-HCl, 10 mM EDTA, pH 8). Inclusion bodies (IBs) were then prepared as described previously (Gertler et al., 1998; Raver et al., 2002) and frozen. Subsequently, IBs obtained from 2.5 l of bacterial culture were solubilized in 300 ml of 4.5 M urea, 40 mM Tris, containing 10 mM cysteine. In the case of ovine leptin or its mutants the IBs obtained from 1.0 l of bacterial culture were solubilized in a similar manner in 200 ml. The pH of the solution was adjusted to 11.5 by NaOH. After 2 h of stirring at 4° C., 3 volumes of 0.67 M arginine were added to a final concentration of 0.5 M and stirred overnight. Next morning, the solution was transferred to dialysis tubes and dialyzed against 5×10 l of 10 mM Tris-HCl, pH 9 (in the case of human leptin mutants) or 10 mM Tris-HCl pH 8 (in the case of ovine leptin mutants), for 60 h, with every 6-10 h external solution exchange.

Example 3

Purification and Chemical Characterization of Leptin Mutants

The refolded and dialyzed fractions of human leptin mutants of Example 2 were purified on a Q-Sepharose anion exchange column (30 ml bead volume), at maximal flow rate (400-500 ml/h), equilibrated with 10 mM Tris-HCl buffer, pH 9, using non continous NaCl gradient (50, 100, 150 and 400 mM of NaCl in 10 mM Tris-HCl,). Fifty-ml fractions were collected and protein concentration was determined by absorbance at 280 nm.

Fractions eluted with 50 mM NaCl, consisting of >95% pure monomer were pooled, dialyzed against $NaHCO_3$, pH 8 at 4:1 protein:salt (w/w) ratio and lyophilized. Ovine leptin mutants were purified in a similar manner using Tris-HCl buffer, pH 8. The yields of human and ovine leptin mutants varied respectively between 160 to 220 mgs, from 2.5 liter of bacterial culture and between 80 to 120 mgs from 1.0 l bacterial culture.

The purity and homogeneity of the purified mutants was documented by three independent methods. Gel filtration at pH 8 under native conditions yielded a single monomeric peak consisting of >95% monomers, corresponding to molecular mass of ~16 kDa (FIG. 1A). In SDS-PAGE under reducing conditions only one band of ~16 kDa was observed (FIG. 1B) and reverse phase chromatography has also yielded single peak (FIG. 1C). The secondary structure of human and ovine leptins and their mutants calculated from the CD spectra are shown in Table 2. High content of α-helix 52-63%, 8-11% β-sheets and 14-18% content of β-turns were clearly characteristic for all the proteins, indicating proper refolding. The only exception was ovine F41A/I42A mutant (SEQ ID NO. 4) in which some disruption of the proper refolding was found. Molar extinction coefficients calculated according to Pace et al. (1995) were used to calculate the specific extinction coefficient at 280 nm for 0.1% solution assuming extra alanine at the N-terminus. The respective values for WT human leptin and the L39A/D40A (SEQ ID NO.1), F41A/I42A (SEQ ID NO. 2), L39A/D40A/F41A (SEQ ID NO. 5) and L39A/D40A/F41A/I42A (SEQ ID NO. 7) mutants were 0.885, 0.890 0.892, 0.895 and 0.897 and corresponding values for ovine species were 0.201, 0.202, 0.202, 0.203 and 0.203. The stability of both human and ovine leptins and their mutants in solution tested at 4°

C. and 37° C. Both wild-type (WT) leptins and their mutants could be stored at both temperatures as sterile 0.1 mM solutions for at least 20 days in pHs 6 or 8 without undergoing any changes in their monomeric content and retaining their activity in the Baf/3 bioassay.

Example 4

Detection of chLBD-leptin or chLBD Mutants-leptin Complex by Gel-filtration

Figure 2:
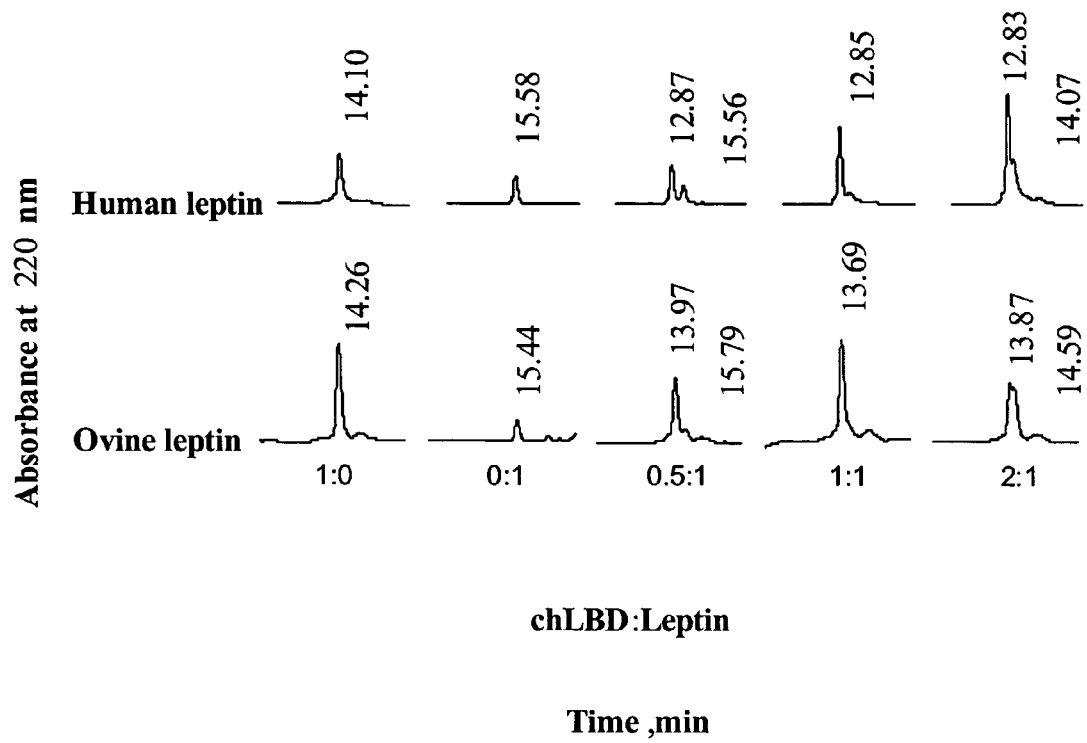

To characterize the binding stoichiometry between human or ovine leptins or their mutants and chLBD the respective ligands and chLBD were mixed in different molar ratios and separated by gel filtration using analytical Superdex 75 column to determine the molecular mass of the binding complex under non-denaturing conditions. The experiments were performed using a constant concentration of 5 µM of the respective ligand and 2.5, 5 or 10 µM of chLBD. The results of chLBD:WT leptins interaction is presented in FIG. 2. The results indicate that both species of leptins bind the chLBD in 1:1 molar ratio. This stoichiometry was determined either by a single peak appearance while the components were mixed at the same molar ratio and an additional peak appearance when there was excess of one of them. The molecular mass calculation of the complex, based on the peak retention time was in all cases ~41 kDa close to the predicted value of 40.5 kDa. Almost identical interaction pattern was also observed with all 8 mutants (not shown) indicating that mutations did not affect the ability of the mutants to form 1:1 complexes with chLBD.

Example 5

Surface Plasmon Resonance (SPR) Determination of the Interaction Between chLBD or its Mutants with Leptin To further characterize the binding capacities of chLBD with human or ovine leptins and their mutants the surface plasmon resonance (SPR) technique using respective leptin (or leptin mutant) immobilized on a sensor chip by amine coupling and binding of soluble chLBD was employed. Results showed that the most acceptable interactions were obtained from comparison to 1:1 theoretical model using $\chi^2$ analysis. The calculated data (mean of 2 experiments) are presented in the Table 3. Though up to 3-fold differences of the kinetic constants were observed the respective Kd values varied to lesser degree and the differences not were statistically significant.

Example 6

Binding Experiments

Figure 3A:
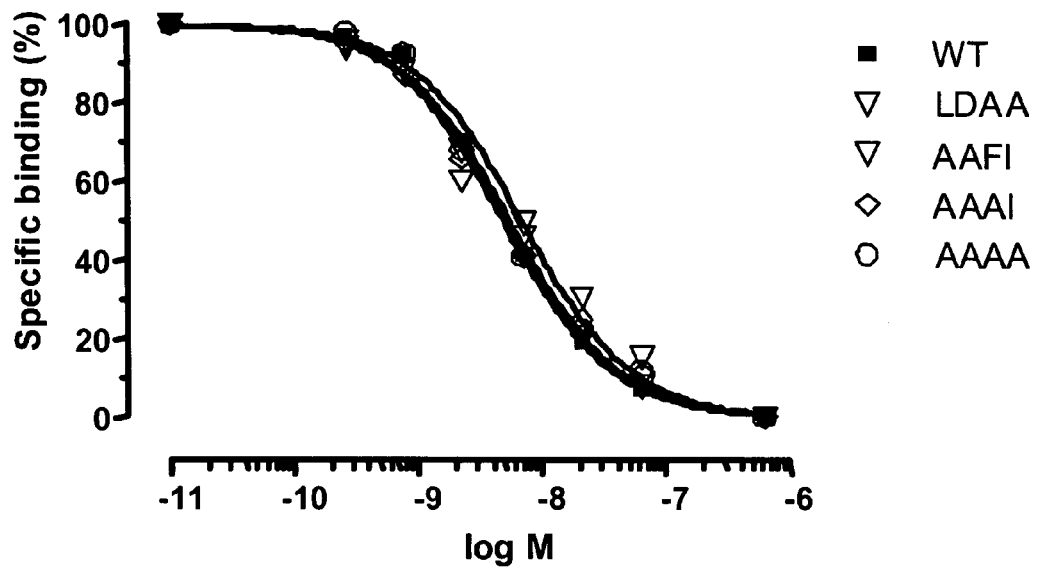
Figure 3B:
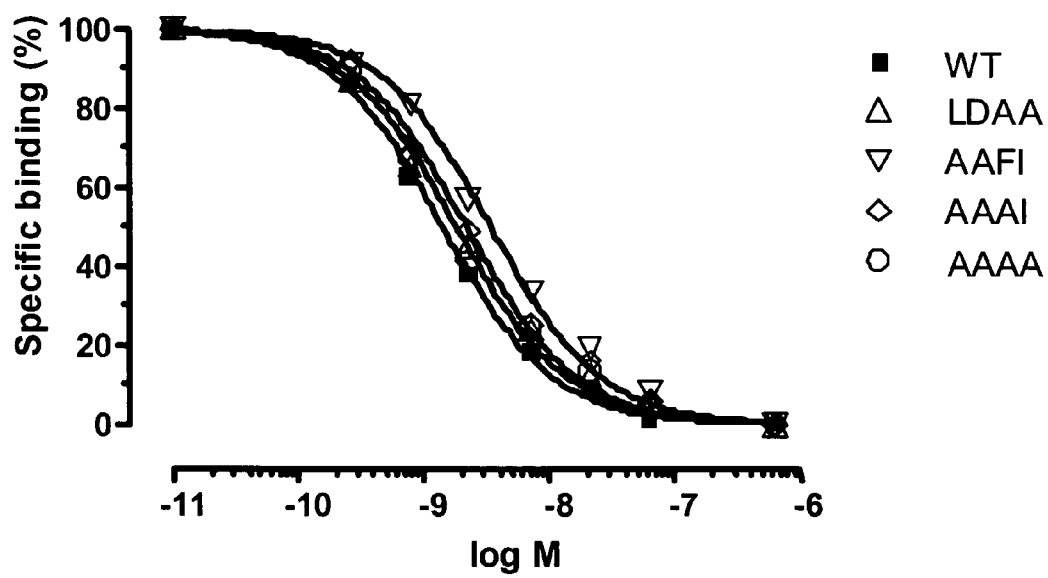

Iodinated human leptin served as the ligand in all competitive experiments and the respective wild-type (WT) human and ovine leptins and their alanine mutants as competitors. Freshly prepared homogenate of BAF/3 cells stably transfected with the long form of human leptin receptor served as receptor source. Homogenate from 1.75× $10^6$ cells was used per tube giving 6 to 7% specific binding. The inhibition curves (average of two experiments) are presented in FIG. 3 and the respective $IC_{50}$ values for WT human leptin and L39A/D40A (SEQ ID NO. 1), F41A/I42A (SEQ ID NO. 2), L39A/D40A/F41A (SEQ ID NO. 5) and L39A/D40A/F41A/I42A (SEQ ID NO. 7) mutants calculated from those curves were 5.33, 4.16, 6.82, 5.21 and 5.43 nM. The corresponding $IC_{50}$ values for WT ovine the respective mutants were 1.47, 1.83, 3.44, 2.20 and 1.83 nM. Minor differences between the leptins and their respective mutants were not significant (P>0.05) except for the F41A/I42A (SEQ ID NO. 2) mutants that had slightly lower (on the border of statistical significance) affinity.

Example 7

Biological Activity in vitro

Figure 4A:
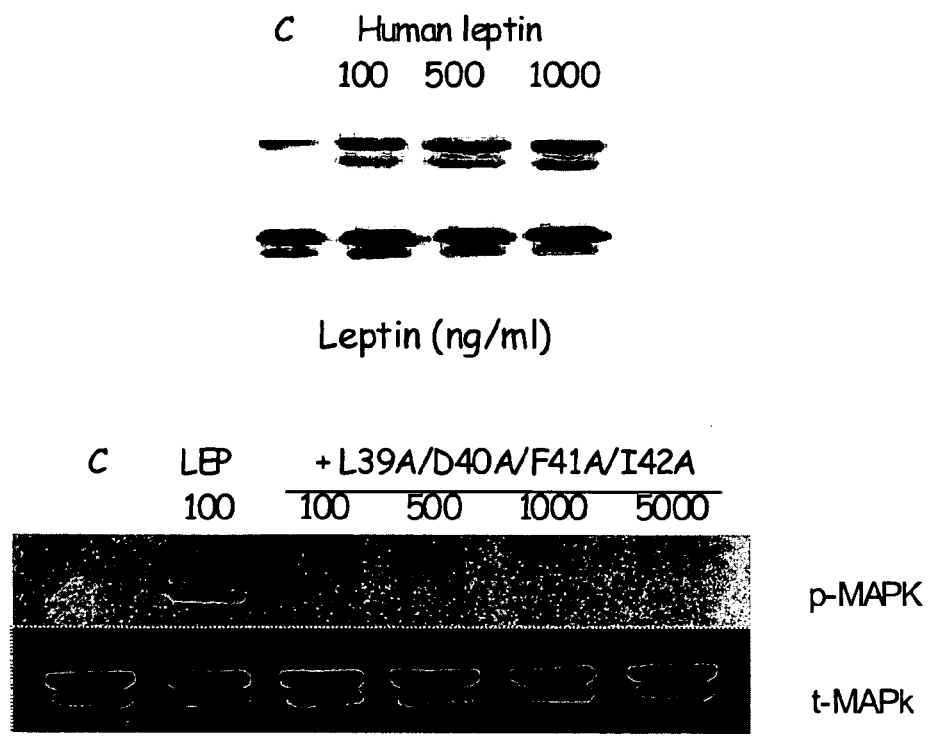
Figure 4B:
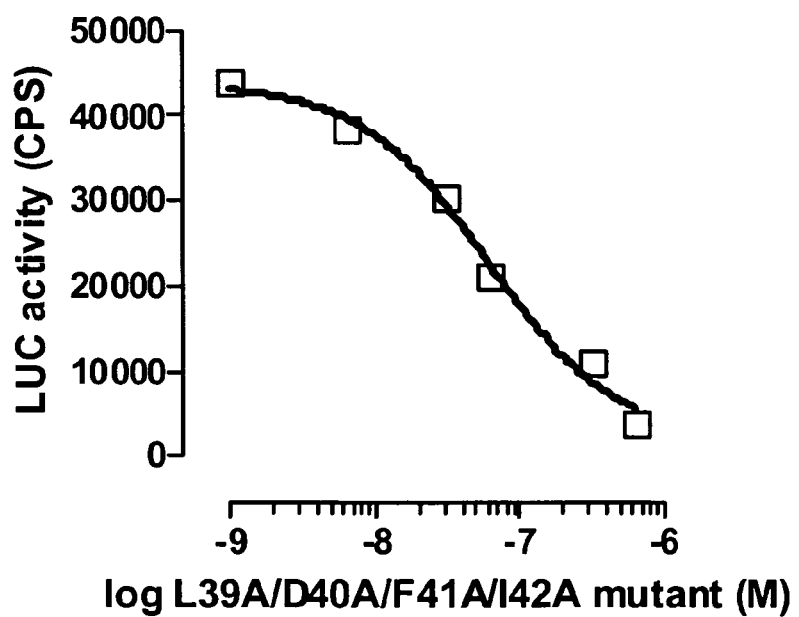

Human and ovine leptin exhibited almost identical activity in Baf/3 bioassay with their respective $EC_{50}$ values of 22 and 37 pM similarly to the results published previously (Raver et al., 2000; Raver et al., 2002). In contrast all four human or ovine leptin mutants were devoid any agonistic activity. To determine the antagonistic activity, BAF/3 cells were stimulated with 62.5 pM human or ovine leptin in the presence (1-125 nM) or absence of the respective mutants. The experiments were repeated 2-7 times and the average $IC_{50}$ values were calculated (Table 4). All 8 mutants exhibited antagonistic activity and no significant differences among human and ovine leptin mutants were observed. The L39A/D40A/F41A (SEQ ID NO. 5) and L39A/D40A/F41A/I42A (SEQ ID NO. 7) mutants were more potent as compared to L39A/D40A (SEQ ID NO. 1) and F41A/I42A (SEQ ID NO. 2). To verify the specificity of inhibition the proliferation of Baf/3 cells was stimulated by IL-3 (55 pM) in the absence or presence of human and ovine leptin mutants. In all eight cases no inhibition was observed even at 125 nM concentration of the mutants. Several leptin mutants were also tested SH-SY5Y human neuroblastoma cells bioassay and by transactivation of luciferase reporting gene in CHO cells transiently transfected with leptin receptor. As shown in FIG. 4A pretreatment with human L39A/D40A/F41A/I42A (SEQ ID NO. 7) leptin antagonist completely blocked the subsequent leptin-inducible activation of MAPK (FIG. 4A) and human L39A/D40A/F41A/I42A (SEQ ID NO. 7) leptin mutant have progressively attenuated the leptin-inducible activation of luciferase (FIG. 4B). Fifty percent inhibition was achieved at approximately ten-fold antagonist to agonist excess.

Example 8

Preparation of Pegylated Leptin Antagonists

The ability of any respective protein to elicit a biological effect in vivo depends on many factors including not only the affinity for its receptor, but also the rate at which it is cleared from circulation. Some hormones, like for example the small atrial natriuretic peptide, are cleared very rapidly ($t_{0.5}$=0.5 min) due to protease-mediated events, whereas others having molecular mass of 15-25 kDa such as leptin (unpublished observations), growth hormone (GH), prolactin and PLs are cleared more slowly ($t_{0.5}$=8-30 min), primarily via the kidney (Johnson et al. 1979; Haffner et al 1994). Since the kidney-mediated clearance is mainly dependent on a molecular mass and proteins larger than 70-80 kDa are cleared at a remarkably slower rate, the effort should be directed at prolongation of hormonal in vivo half-live by increasing its size. This can be achieved by increasing the size of the hormone without affecting its activity by pegylation. Attachment of several polyethylene glycol (PEG) molecules increases the hydrodynamic volume of the protein, thereby slowing its clearance (Abuchowski et al.; 1977). One of the most surprising results considering pegylated human growth hormone (hGH) was the recent finding that despite the up to 500-fold lower affinity and in vitro activity, the in vivo potency of the pegylated hGH was remarkably increased mainly due to up to 25-fold increase in its half-life in the circulation. Thus, it was concluded that increasing circulating half-life can compensate the deficits in receptor binding affinity (Clark et al., 1996).

Pegylation is performed by cross-linking of the purified leptin mutants with polyethylene glycol (MW 4-6 kDa) to alpha- or epsilon-amino groups by well known procedures (Clark et al., 1996). Our results using ovine leptin indicated that pegylation did not decrease the biological activity of leptin (Raver and Gertler, unpublished results). Those results prompt us to anticipate that pegylation of leptin mutants will also not affect their ability to interact with leptin receptors and subsequently their antagonistic capacity. Thus, the beneficial effects of the leptin mutants may be prolonged in vivo by pegylation or any other slow release formulation.

Discussion and Summary of Results

Class I cytokines interact with their receptor through conserved binding sites (sites I and II). G-CSF and cytokines of the gp130 family, including IL-6 have an additional binding site (site III), which was shown in recent crystal structures of IL-6-gp130 complexes to interact with the Ig-like domain (IGD) of the receptor (Chow et al., 2001; Boulanger et al., 2003) in a 2:2 arrangement. A similar type of complex formation is expected for the leptin/leptin receptor interaction due to the sequence similarities and overall architecture that the two interacting partners share with the hormone and receptors of the G-CSF and gp130 family of cytokines. (Zabeau et al., 2004; Peelman et al., 2004). We thus modelled the leptin receptor IGD domain on the basis of the gp130 IGD structure (pdb code 1i1r; Chow et al., 2001), and fitted this model on the gp130-vIL-6 complex. The experimental structure of leptin, as observed isolated (pdb code 1ax8; Zhang et al., 1997), was fitted on the vIL-6 structure, based on four conserved blocks corresponding to the α-helices.

As observed in the structures of the vIL-6-gp130 (pdb 1i1r; Chow et al., 2001) shown in FIG. 5, top panel and IL-6-gp130-IL-6R (pdb 1p9m; Boulanger et al., 2003) complexes, site III includes the N-terminus of helix D (dark blue), loop C-D (light blue) and loop A-B (orange) and contacts the IGD of the receptor (gray on the left part of the figure). Site III appears to be the most variable region amongst the cytokines. Notably, the A-B loop (orange in FIG. 5) is of variable length and, in the isolated structure of human leptin (pdb 1ax8; Zhang et al., 1997) or even in the IL-6-gp130-IL-6R (pdb 1p9m; Boulanger et al., 2003), appears to be disordered, no residues being visible in the electron density map. Loop C-D is also variable (light blue in FIG. 5). Remarkably, in the vIL-6-gp130 complex (pdb 1i1r;. Chow et al., 2001), the A-B loop includes a short β-strand, which forms a β-sheet-like structure through mainchain H-bonds with the first β-strand of the receptor D1 domain (FIG. 6, top panel). Moreover, an extended, β-strand-like structure can also be observed between the C-terminus of helix A and this β-strand, leading to a relatively flat contact surface with one of the two β-sheet of the receptor D1 domain (FIG. 6).

Assuming the leptin site III interaction with IGD of LEPR resembles that of IL-6, despite a great sequence divergence, we have utilized the Hydrophobic Cluster Analysis (HCA) for predicting regular secondary structures, which might be present in the leptin AB loop. This two-dimensional method allows the accurate prediction of secondary structures from the knowledge of a single sequence (Gaboriaud et al., 1987; Callebaut et al., 1997; Hennetin et al., 2003). FIG. 6 provides the 2D-representations of human leptin and viral IL-6 (1IR1). The highlighted hydrophobic clusters mainly correspond to the regular secondary structures of the considered proteins. In the two proteins, a loop of variable length separates helix A from helix B. However, in the IL-6 this loop includes clusters, which are typical of extended (β-strand) structures. The middle one corresponds to the β-strand, which interacts with the IGD of g130. The situation is different for leptin, and even simpler, as the loop is shorter and contains only one cluster, typical of a β-strand structure (VTGLDFI/S (SEQ ID NO:34); cluster associated at 77% with β-strands (our unpublished statistics)). It can be thus tentatively aligned to the IGD-interacting β-strand of IL-6, the sequence of which is LEPAAIF (SEQ ID NO:35).

Modeling of the corresponding interface in leptin, which is partially missing in the crystal structure of the isolated molecule (dashed orange line in FIG. 5, bottom panel), was however not possible due to the lack of an appropriate template for the AB loop, as well as due to the fact that a conformational change probably occurs in the neighboring CD loop upon receptor recognition.

Figure 5:
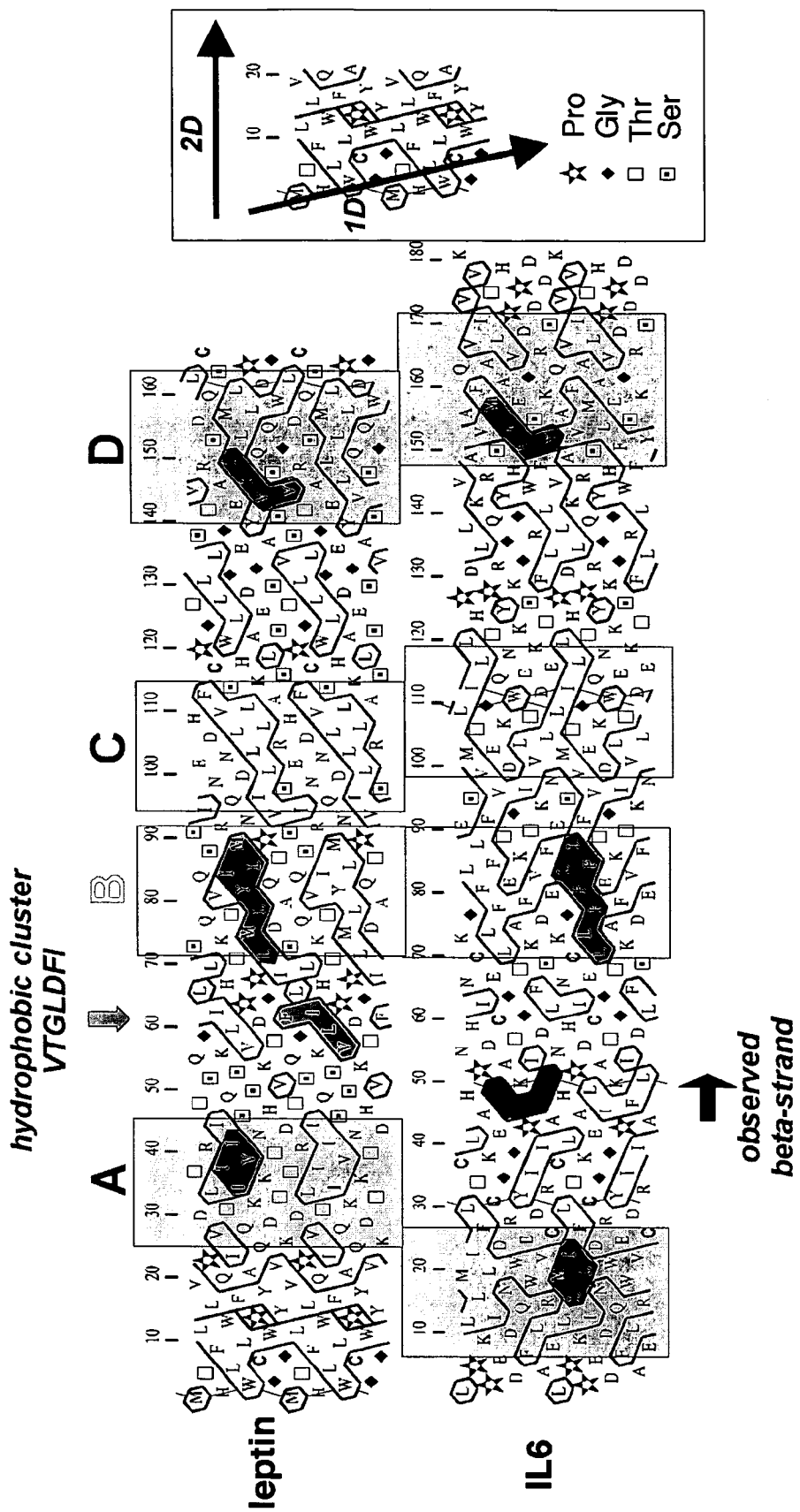

On another hand, the core of the interface of viral IL-6 with gp130 and involving loop CD is formed by the three aromatic amino acids Tyr143, Trp144 and Phe148 (Chow et al., 2001, FIG. 5, top panel, highlighted in violet). Although no aromatic residue is present in strictly equivalent positions in leptin, a tyrosine residue (Tyr119, pink in FIG. 6, bottom panel) might play a similar role in the interaction with the leptin receptor. To test this assumption we have mutated this residue to Ala and prepared the recombinant mutant Y119A. Despite correct refolding as indicated by CD spectrum this mutant exhibited substantially lower agonistic activity and was totally devoid of any antagonistic effect (unpublished data).

Therefore we considered the conserved β-strand of the leptin AB loop, which is thought to form intermolecular association with one of the β-sheet of the receptor IGD as a target and mutated the LDFI/S (residues 4-7 of SEQ ID NO:34) (aa 39-42) fragment. Since preparing R128Q leptin mutant we have formerly observed that the effect of mutation may be species-dependent (Raver et al., 2002) all present mutations were carried out simultaneously in human and ovine leptins. Eight mutants (four human and four ovine) were prepared in good yield. All mutants were purified to homogeneity as evidenced by gel filtration, SDS-PAGE and reverse phase chromatography (FIG. 1) and consisted of >95% monomers. Structural analysis of the secondary structure revealed proper refolding except for ovine L39A/D40A (SEQ ID NO:3) mutant (Table 2). All eight mutants acted as true antagonists namely they interacted with LEPR with the affinity similar to the wild type hormone as evidenced by SPR and RRA (Table 3, FIG. 3), formed a 1:1 complex with chLBD similarly to the WT leptins, were devoid biological activity in Baf/3 leptin-responsive bioassay and specifically inhibited leptin action (Table 4). Human L39A/D40A/F41A/I42A (SEQ ID NO. 7) mutant had also inhibited leptin-inducible activity in other in vitro bioassays (FIG. 4).

TABLE 2

Secondary structure of human and ovine leptins and their alanine mutants at neutral pH

| Protein tested[1] | $[\theta]_{222}$[2] | α-Helix, % | β-Sheets, % | β-Turns, % | Random, % |
|---|---|---|---|---|---|
| Human mutants | | | | | |
| Wild type | −21.0 ± 0.8 | 63 ± 0.6 | 8 ± 1.1 | 17 ± 0.6 | 12 ± 1.5 |
| L39A/D40A | −21.2 ± 0.8 | 63 ± 0.6 | 8 ± 1.0 | 16 ± 0.5 | 13 ± 1.2 |
| F41A/I42A | −20.3 ± 0.7 | 60 ± 0.6 | 8 ± 1.0 | 16 ± 0.6 | 15 ± 1.4 |
| L39A/D40A/F41A | −18.8 ± 0.8 | 53 ± 0.5 | 11 ± 0.8 | 18 ± 0.4 | 24 ± 0.7 |
| L39A/D40A/F41A/I42A | −20.4 ± 0.7 | 59 ± 0.6 | 7 ± 1.0 | 16 ± 0.5 | 18 ± 1.3 |
| Ovine mutants | | | | | |
| Wild type | −21.1 ± 0.8 | 60 ± 0.5 | 4 ± 0.9 | 15 ± 0.5 | 22 ± 1.1 |
| L39A/D40A | −18.4 ± 1.1 | 52 ± 0.4 | 8 ± 0.7 | 14 ± 0.4 | 26 ± 0.8 |
| F41A/I42A | −12.7 ± 0.4 | 37 ± 0.4 | 19 ± 0.7 | 20 ± 0.4 | 24 ± 0.7 |
| L39A/D40A/F41A | −21.9 ± 0.8 | 62 ± 0.5 | 5 ± 0.8 | 14 ± 0.4 | 18 ± 1.0 |
| L39A/D40A/F41A/I42A | −20.9 ± 0.6 | 57 ± 0.4 | 5 ± 0.8 | 14 ± 0.4 | 24 ± 0.9 |

[1]The results are given as means ± SD. The errors arose only from an uncertainty of the fitting of the experimental CD spectrum by the set of standard protein CD spectra in the CONTIN program. The errors of both, the CD measurments and the protein concentration determination were not included.
[2]$[\theta]_{222}$ is molar ellipticity per mol of residue and in kdeg cm$^2$dmol$^{-1}$.

TABLE 3

Calculation of kinetic and thermodynamic constants for the interaction of WT leptins and their mutants with immobilized chLBD measured by surface plasmon resonance (SPR).

| Mutant | $k_{on}$ (mol$^{-1}$s$^{-1}$ × 10$^5$) | $k_{off}$ (sec$^1$ × 10$^{-3}$) | Kd (M × 10$^{-8}$) | Chi square[2] |
|---|---|---|---|---|
| Human leptin mutants[1] | | | | |
| WT leptin | 1.49 ± 0.34 | 4.3 ± 0.1 | 2.88 ± 0.53 | 1.71-1.87 |
| L39A/D40A | 5.45 ± 0.55 | 12.5 ± 1.5 | 2.29 ± 0.09 | 3.15-3.83 |
| F41A/I42A | 3.62 ± 0.15 | 11.5 ± 0.4 | 3.18 ± 0.21 | 1.73-4.29 |
| L39A/D40A/F41A | 3.58 ± 0.54 | 10.2 ± 0.8 | 2.85 ± 0.48 | 2.53-4.73 |
| L39A/D40A/F41A/I42A | 1.35 ± 0.47 | 6.8 ± 1.0 | 5.03 ± 3.96 | 0.43-0.54 |
| Ovine leptin mutants[1] | | | | |
| WT leptin | 1.62 ± 0.94 | 3.7 ± 0.8 | 2.28 ± 2.15 | 0.58-1.57 |
| L39A/D40A | 2.37 ± 0.03 | 5.7 ± 0.1 | 2.40 ± 0.06 | 2.31-5.18 |
| F41A/I42A | 2.50 ± 0.15 | 3.2 ± 0.2 | 1.28 ± 0.03 | 1.80-3.54 |
| L39A/D40A/F41A | 1.81 ± 0.06 | 2.5 ± 0.2 | 1.38 ± 0.13 | 1.74-4.57 |
| L39A/D40A/F41A/I42A | 1.09 ± 0.18 | 3.2 ± 0.1 | 2.93 ± 0.56 | 1.24-3.18 |

[1]mean of 2 experiments ± SD
[2]lower values indicate better fit

TABLE 4

Antagonistic activity of human and ovine leptin mutants in BAF/3 cells stably transfected with long form of LEPR.

| | IC$_{50}$ (nM), mean ± SEM[2] | |
|---|---|---|
| Leptin mutant[1] | h-leptin | o-leptin |
| L39A/D40A | 17.7 ± 3.76 (4) | 41.8 ± 14.1 (7) |
| F41A/I42A | 15.6 ± 3.87 (4) | 31.0 ± 19.9 (3) |
| L39A/D40A/F41A | 10.0 ± 0.90[3] (2) | 17.1 ± 4.4 (3) |
| L39A/D40A/F41A/I42A | 9.3 ± 1.60 (5) | 9.5 ± 4.6 (3) |

[1]cells were stimulated with 0.0625 nM leptin,
[2]the numbers in parentheses indicate the number of performed experiments,
[3]mean ± SD.

In order to compare the activity of our mutants to the recently reported S120A/T121A human leptin mutant which exhibited antagonistic activity (Peelman et al 2004) we have prepared and purified to homogeneity two additional human leptin mutants: S120A/T121A and L39A/D40A/F41A/I42A/S120A/T121A. Both mutants bound to chLBD with the respective affinity of 2.95×10$^{-8}$ M and 2.69×10$^{-8}$ M similar to that of the WT human leptin (2.88×10$^{-8}$ M). However in the Baf/3 bioassay the S120A/T121A mutant exhibited low agonistic activity and the IC$_{50}$ for inhibition was over 150-higher as compared to either L39A/D40A/F41A or L39A/D40A/F41A/I42A (165±81 nM, mean±SEM of 5 experiments, vs 10.0 and 9,3 nM as shown in Table 4), indicating lower antagonistic activity. In contrast the IC$_{50}$ value for the L39A/D40A/F41A/I42A/S120A/T121A (14.3±1.34, mean±CD of 2 experiments) was comparable to L39A/D40A/F41A or L39A/D40A/F41A/I42A mutants. Thus we conclude that the mutants of the present invention are superior to S120A/T121A mutant and combination of both mutations has no advantage.

In conclusion, the mutants of the present invention act as competitive antagonists to leptin. Those mutants can be easily prepared in gram amounts and thus serve as a novel tool of studying leptin function in vitro and in vivo. Furthermore, antagonizing leptin has been suggested as a possible therapy in auto-immune diseases and might also have beneficiary effects on atherosclerosis. Thus leptin antagonists offer a novel tool to elucidate the role of leptin in mammalian physiology and pathology.

REFERENCES

Abuchowski, A., McCoy, J. R., Palczuk, N. C., Van Es, T. and Davis, F. F. (1977) Effect of covalent attachment of polyethylene glycol on immunogenicity and circulating life of bovine liver catalase. *J. Biol. Chem.* 252, 3582-3586.

Aritomi, M., Kunishima, N., Okamoto, T., Kuroki, R., Ota, Y., and Morikawa, K. (1999) Atomic structure of the GCSF-receptor complex showing a new cytokine-receptor recognition scheme. *Nature* 401, 713-7.

Bignon, C., Daniel, N., and Djiane, J. (1993) Beta-galactosidase and chloramphenicol acetyltransferase assays in 96-well plates. *BioTechniques* 15, 243-246.

Boulanger, M. J., Chow, D. C., Brevnova, E. E., and Garcia, K. C. (2003) Hexameric structure and assembly of the interleukin-6/IL-6 α-receptor/gp130 complex. *Science* 300, 2101-104.

Briscoe, C. P., Hanif, S., Arch, J. R., and Tadayyon, M. (2001) Leptin receptor long-form signalling in a human liver cell line. *Cytokine* 14, 225-9.

Callebaut, I., Labesse, G., Durand, P., Poupon, A., Canard, L., Chomilier, J., Henrissat, B., Mornon, J. P. (1997) Deciphering protein sequence information through hydrophobic cluster analysis (HCA): current status and perspectives. *Cell Mol Life Sci* 53, 621-645.

Choi J H, Park S H, Leung P C, Choi K C. (2004) Expression of Leptin Receptors and Potential Effects of Leptin on the Cell Growth and Activation of Mitogen-activated Protein Kinases in Ovarian Cancer Cells. *J Clin Endocrinol Metab.* 2004 Nov. 2; [Epub ahead of print].

Chow, D., He, X., Snow, A. L., Rose-John, S., and Garcia, K. C. (2001) Structure of an extracellular gp130 cytokine receptor signaling complex. *Science* 291, 2150-2155.

Cioffi, J. A., Shafer, A. W., Zupancic, T. J., Smith-Gbur, J., Mikhail, A., Platika, D., and Snodgrass, H. R. (1996) Novel B219/OB receptor isoforms: possible role of leptin in hematopoiesis and reproduction. *Nat Med.* 2, 585-9.

Clark, R., Olson, K., Fuh, G., Mariuan, M., Mortensen, D., Teshima, G., Chang., S., Chu, H., Mukku, V., Canova-Davis, E., Sommers, T., Cronin, M., Winkler, M. and Wells, J. A. (1996). Long-acting growth hormones produced by conjugation with polyethylene glycol. *J. Biol. Chem.* 271: 21969-21977.

Dagogo-Jack S, Fanelli C, Paramore D, Brothers J, and Landt M. (1996) Plasma leptin and insulin relationships in obese and nonobese humans. *Diabetes.* 45(5):695-698.

De Vos, A. M., Ultsch, M., and Kossiakoff, A. A. (1992) Human growth hormone and extracellular domain of its receptor: crystal structure of the complex. *Science* 255, 306-312.

Emilsson, V., Liu, Y. L., Cawthorne, M. A., Morton, N. M., and Davenport, M. (1997) Expression of the functional leptin receptor mRNA in pancreatic islets and direct inhibitory action of leptin on insulin secretion. *Diabetes* 46, 313-6.

Frankenberry K A, Somasundar P, McFadden D W, Vona-Davis L C. (2004) Leptin induces cell migration and the expression of growth factors in human prostate cancer cells. *Am J Surg.* 188(5):560-5.

Friedman, J. M, and Halaas, J. L. (1998) Leptin and the regulation of body weight in mammals. *Nature* 395, 763-70.

Fong, T. M., Huang, R. R., Tota, M. R., Mao, C., Smith, T., Varnerin, J., Karpitskiy, V. V., Krause, J. E., and Van der Ploeg, L. H. (1998) Localization of leptin binding domain in the leptin receptor. *Mol. Pharmacol.* 53, 234-40.

Gaboriaud, C., Bissery, V., Benchetrit, T. Mornon, J.-P. (1987) Hydrophobic cluster analysis: an efficient new way to compare and analyse amino acid sequences. *FEBS Lett.* 224, 149-155.

Gertler, A., Ashkenazi, A., and Madar, Z. (1984) Binding sites of human growth hormone and ovine and bovine prolactins in the mammary gland and the liver of lactating dairy cow. *Mol. Cell. Endocrinol.* 34, 51-7.

Gertler, A., Simmons, J., and Keisler, D. H. (1998) Large-scale preparation of biologically active recombinant ovine obese protein (leptin). *FEBS Lett.* 422, 137-40.

Glasow, A., Haidan, A., Hilbers, U., Breidert, M., Gillespie, J., Scherbaum, W. A., Chrousos, G. P., and Bornstein, S. R. (1998) Expression of Ob receptor in normal human adrenals: differential regulation of adrenocortical and adrenomedullary function by leptin. *J. Clin. Endocrinol. Metab.* 83, 4459-66.

Haffner, D., Schaefer, F., Girard, F., Ritz, E. and Mehls, (1994) Metabolic clearance of recombinant human growth hormone in health and chronic renal failure. *J. Clin. Invest.* 93, 1163-1171.

Hennetin, J., LeTuan, K., Canard, L., Colloc'h, N., Mornon, J.-P., Callebaut, I. (2003) Non-intertwined binary patterns of hydrophobic/nonhydrophobic amino acids are considerably better markers of regular secondary structures than nonconstrained patterns. *Proteins* 51, 236-244.

Hoggard, N., Hunter, L., Duncan, J. S., Williams, L. M., Trayhurn, P., and Mercer, J. G. (1997) Leptin and leptin receptor mRNA and protein expression in the murine fetus and placenta. *Proc. Natl. Acad. Sci. USA* 94, 11073-8.

Johnsson, B, Lofas, S., and Lindquist, G. (1991) Immobilization of proteins to a carboxymethyldextran-modified gold surface for biospecific interaction analysis in surface plasmon resonance sensors. *Anal. Biochem.* 198, 268-77.

Johnson, V. and Maackt. (1979) Renal extraction, filtration, absorption, and catabolism of growth hormone. *Am. J. Physiol.* 233:185-19

Laemmli, U. K. (1970) Cleavage of structural proteins during the assembly of the head of bacteriophage T4. *Nature,* 227, 680-5.

Livnah. O., Stura, E. A., Middleton, S. A., Johnson, D. L., Jolliffe, L. K., and Wilson, I. A. (1999) Crystallographic evidence for preformed dimers of erythropoietin receptor before ligand activation. *Science* 283, 987-90.

Muller-Newen, G. (2003) The cytokine receptor gp130: faithfully promiscuous. *Science STKE.* (201) PE40.

Pace, C. N., Vajdos, F., Fee, L., Grimsley, G., and Gray, T. (1995) How to measure and predict the molar absorption coefficient of a protein. *Protein Sci.* 4, 2411-23.

Peelman, F., Van Beneden, K., Zabeau, L., Iserentant, H., Ulrichts, P., Defeau. D., Verhee, A., Catteeuw, D., Elewaut, D., and Tavernier, J. (2004) Mapping of the leptin binding sites and design of a leptin antagonist. *J. Biol. Chem.* 279, 41038-46.

Pelleymounter M A, Cullen M J, Baker M B, Hecht R, Winter D, Boone T, and Collins F. (1995) Effects of the obese gene product on body weight regulation in ob/ob mice. *Science* 269, 540-543.

Prisma (2003) GraphPad Prism™ Version 4.0 GraphPad Software Inc., San Diego, Calif., USA.

Provencher, S. W. and Glöckner, J. (1981) Estimation of globular protein secondary structure from circular dichroism. *Biochemistry* 20, 33-7.

Raver, N., Gussakovsky, E. E., Keisler, D. H., Krishna, R., Mistry, J., and Gertler, A. (2000) Preparation of recombinant bovine, porcine, and porcine W4R/R5K leptins and comparison of their activity and immunoreactivity with ovine, chicken, and human leptins. *Protein Expr. Purif.* 19, 30-40.

Raver, N., Vardy, E., Livnah, O., Devos, R., and Gertler, A. (2002) Comparison of R128Q mutations in human, ovine, and chicken leptins. *Gen. Comp. Endocrinol.* 126, 52-8.

Raver, N., Sandowski, Y., Sakal, E., Shochat, S., Livnah, O., Einat, M., and Gertler, A. (2003) Recombinant human and chicken leptin-binding domains derived from respective leptin receptors, *Experimental Biology Meeting*, Apr. 11-15, 2003. San Diego, Calif., abstract no. 1209.

Sandowski, Y., Raver, N., Gussakovsky, E. E., Shochat, S., Dym, O., Livnah, O., Rubinstein, M., Krishna, R., and Gertler, A. (2002) Subcloning, expression, purification, and characterization of recombinant human leptin-binding domain. *J. Biol. Chem.* 277, 46304-9.

Sreerama, S., and Woody, R. W. (1993) A self-consistent method for the analysis of protein secondary structure from circular dichroism. *Anal. Biochem.* 209, 32-44.

Somasundar P, Frankenberry K A, Skinner H, Vedula G, McFadden D W, Riggs D, Jackson B, Vangilder R, Hileman S M, Vona-Davis L C. (2004) Prostate cancer cell proliferation is influenced by leptin. *J Surg Res.* 118(1):71-82.

Sotiropoulos, A., Moutoussamy, S., Renaudie, F., Clauss, M., Kayser, C., Gouilleux, F., Kelly, P. A., and Finidori, J. (1996) Differential activation of Stat3 and Stat5 by distinct regions of the growth hormone receptor. *Mol. Endocrinol.* 10, 998-1009.

Venyaminov, S. Yu., and Yang, J. T. (1996) Determination of secondary structure. In: *Circular Dichroism and the Conformational analysis of Biomolecules* (Fasman, G. D., Ed.) pp. 69-107, Plenum Press, New York.

Wells, J. A., and De Vos, A. M. (1996) Hematopoietic receptor complexes. *Annu. Rev. Biochem.* 65, 609-34.

Zabeau, L., Defeau, D., Van der Heyden, J., Iserentant, H., Vandekerckhove, J., and Tavernier, J. (2004) *Mol. Endocrinol.* 18, 150-61.

Zhang, F., Basinski, M. B., Beals, J. M., Briggs, S. L., Churgay, L. M., Clawson, D. K., DiMarchi, R. D., Furman. T. C., Hale, J. E., Hsiung, H. M., Schoner, B. E., Smith, D. P., Zhang, X. Y., Wery, J-P., and Schweitz, R. W. (1997). Crystal structure of the obese protein leptin-E100. *Nature* (London) 387, 206-209.

The invention claimed is:

1. A leptin antagonist consisting of:
   (a) a mammalian leptin polypeptide in which the LDFI (SEQ ID NO:33) hydrophobic binding site at the positions corresponding to positions 39-42 of the wild-type human leptin, is modified such that from two to four amino acid residues of said hydrophobic binding site are substituted with different amino acid residues such that the site becomes less hydrophobic, said modified, mammalian leptin polypeptide being a leptin antagonist; or
   (b) a fragment of said modified mammalian leptin polypeptide of (a) comprising said altered hydrophobic binding site, wherein said fragment is itself a leptin antagonist.

2. A leptin antagonist of claim 1, wherein said two to four amino acid residues of the SEQ ID NO:33 are substituted with amino acids selected from the group consisting of alanine, arginine, aspartic acid, glutamic acid, glycine, lysine and serine.

3. A leptin antagonist of claim 2, wherein said amino acid is alanine.

4. A leptin antagonist of claim 1, wherein two of the four amino acid residues the SEQ ID NO:33 are substituted with alanine.

5. A leptin antagonist of claim 4, wherein said modified mammalian leptin is modified human leptin.

6. A leptin antagonist of claim 5, consisting of the polypeptide of SEQ ID NO: 1 or SEQ ID NO: 2.

7. A leptin antagonist of claim 4, wherein said modified mammalian leptin is modified ovine leptin.

8. A leptin antagonist of claim 7, consisting of the polypeptide of SEQ ID NO: 3 or SEQ ID NO: 4.

9. A leptin antagonist of claim 1, wherein three of the amino acid residues at any of said positions 39-42 are substituted with alanine.

10. A leptin antagonist of claim 9, wherein said modified mammalian leptin is modified human leptin.

11. A leptin antagonist of claim 10, consisting of the polypeptide of SEQ ID NO: 5.

12. A leptin antagonist of claim 9, wherein said modified mammalian leptin is modified ovine leptin.

13. A leptin antagonist of claim 12, consisting of the polypeptide of SEQ ID NO: 6.

14. A leptin antagonist of claim 1, wherein all four amino acid residues at said positions 39-42 are substituted with alanine.

15. A leptin antagonist of claim 14, consisting of the polypeptide of SEQ ID NO:7 or SEQ ID NO: 8.

16. An isolated DNA molecule encoding a leptin antagonist of claim 1.

17. A DNA molecule of claim 16 selected from the group consisting of the DNA sequences of SEQ ID NOs: 9, 10, 11, 12, 13, 14, 15 and 16.

18. A leptin antagonist of claim 1, consisting of a fragment of (b).

19. A leptin antagonist of claim 1 in pegylated form.

20. A pharmaceutical composition comprising a leptin antagonist of claim 1 and a pharmaceutically acceptable carrier.

21. The pharmaceutical composition of claim 20, wherein the leptin antagonist is in a pegylated form.

* * * * *